United States Patent
Mehta et al.

(10) Patent No.: US 10,813,938 B2
(45) Date of Patent: Oct. 27, 2020

(54) POLYMORPHS OF COCRYSTALS OF EPIGALLOCATECHIN GALLATE AND CAFFEINE

(71) Applicant: AMRI SSCI, LLC, West Lafayette, IN (US)

(72) Inventors: Shital Viral Mehta, Lafayette, IN (US); Jing Teng, West Lafayette, IN (US); Jon Selbo, West Lafayette, IN (US)

(73) Assignee: AMRI SSCI, LLC, West Lafayette, IN (US)

( * ) Notice: Subject to any disclaimer, the term of this patent is extended or adjusted under 35 U.S.C. 154(b) by 0 days.

(21) Appl. No.: 15/756,213

(22) PCT Filed: Sep. 1, 2016

(86) PCT No.: PCT/US2016/049941
§ 371 (c)(1),
(2) Date: Feb. 28, 2018

(87) PCT Pub. No.: WO2017/040809
PCT Pub. Date: Mar. 9, 2017

(65) Prior Publication Data
US 2018/0289715 A1    Oct. 11, 2018

Related U.S. Application Data

(60) Provisional application No. 62/245,215, filed on Oct. 22, 2015, provisional application No. 62/212,713, filed on Sep. 1, 2015.

(51) Int. Cl.
| | | |
|---|---|---|
| *A61K 31/522* | (2006.01) | |
| *A61K 31/353* | (2006.01) | |
| *C07D 311/74* | (2006.01) | |
| *C07D 473/12* | (2006.01) | |
| *A23L 33/105* | (2016.01) | |

(52) U.S. Cl.
CPC .......... *A61K 31/522* (2013.01); *A23L 33/105* (2016.08); *A61K 31/353* (2013.01); *C07D 311/74* (2013.01); *C07D 473/12* (2013.01); *A23V 2002/00* (2013.01)

(58) Field of Classification Search
CPC .................................................. A61K 31/522
See application file for complete search history.

(56) References Cited

U.S. PATENT DOCUMENTS

2010/0204204 A1    8/2010    Zaworotko et al.

OTHER PUBLICATIONS

PCT International Search Report and Written Opinion corresponding to PCT/US2016/049941, dated Oct. 28, 2016.

*Primary Examiner* — Brian E McDowell
(74) *Attorney, Agent, or Firm* — Troutman Pepper Hamilton Sanders LLP (Rochester)

(57) ABSTRACT

Described herein are cocrystals of epigallocatechin gallate (ECGC) and caffeine, compositions comprising such cocrystals, methods of making such cocrystals, and methods of improving animal or human health by treating with such cocrystals. In particular, Form I and Form II of a 1:2 (epigallocatechin gallate to caffeine) cocrystal are described.

8 Claims, 29 Drawing Sheets

POLYMORPHS OF COCRYSTALS OF EPIGALLOCATECHIN GALLATE AND CAFFEINE

This application is a national stage application under 35 U.S.C. § 371 of PCT Application No. PCT/US2016/049941, filed Sep. 1, 2016, which claims the priority benefit of U.S. Provisional Patent Application Ser. No. 62/212,713, filed Sep. 1, 2015, and U.S. Provisional Patent Application Ser. No. 62/245,215, filed Oct. 22, 2015, both of which are hereby incorporated by reference in their entirety.

FIELD OF THE INVENTION

The present invention relates to cocrystals of epigallocatechin gallate and caffeine.

BACKGROUND OF THE INVENTION

Epigallocatechin gallate ("EGCG"), a polyphenol compound and antioxidant found in green tea, has lately received considerable attention for its health beneficial properties. EGCG has been studied for multiple therapeutic pathways, including for the prevention of cancer and cardiovascular diseases. EGCG is available commercially in dietary supplements. However, EGCG has limited bioavailability on oral intake.

Caffeine, a central nervous system stimulant, is a model pharmaceutical compound used as an additive in multiple food and drug formulations. Caffeine is known to exhibit in two anhydrous crystal forms and one non-stoichiometric hydrate form. It is unstable with respect to relative humidity and converts to the non-stoichiometric hydrate.

Hydrates of EGCG acid have previously been published. For example, U.S. Pat. No. 8,471,044 and Smith et al., "Crystal Engineering of Green Tea Epigallocatechin-3-gallate (EGCg) Cocrystals and Pharmacokinetic Modulation in Rats," *Mol. Pharmaceutics* 10:2948-2961 (2013) disclose crystalline forms of EGCG including hydrates.

Modification of the bioavailability of EGCG has been attempted by conventional preformulation techniques such as nanolipid particle generation and crystal engineering.

Cocrystallization of EGCG with isonicotinamide has previously demonstrated reduced solubility and a slightly higher bioavailability.

Caffeine cocrystals of other compounds have previously been reported in the literature. For example, U.S. Pat. No. 8,318,804 discloses cocrystals of caffeine with pterostilbene.

A cocrystal of a compound is a distinct chemical composition between the compound and coformer, and generally possesses distinct crystallographic and spectroscopic properties when compared to those of the compound and coformer individually. A coformer is also a compound and is often referred to as a "guest." The compound which is not the coformer is often referred to as the "host." Unlike salts, which possess a neutral net charge, but which are comprised of charge-balanced components, cocrystals are comprised of neutral species. Thus, unlike a salt, one cannot determine the stoichiometry of a cocrystal based on charge balance. Indeed, one can often obtain cocrystals having molar ratios of compound to coformer of greater than or less than 1:1. The molar ratio of the components is a generally unpredictable feature of a cocrystal.

Cocrystals have the potential to alter physicochemical properties. More specifically, cocrystals have been reported to alter aqueous solubility and/or dissolution rates, increase stability with respect to relative humidity, and improve bioavailability of active pharmaceutical ingredients with respect to other cocrystals of such ingredients. The coformer, or guest, is often varied or selected for purposes of altering such properties.

The chemical composition of a cocrystal, including the molar relationship between the coformer and the compound (such as an active pharmaceutical ingredient (API)) can be determined by single crystal x-ray analysis. Where such an analysis is not available, often solution-state proton NMR is used to verify composition and identify molar ratio.

Cocrystal formation may be further confirmed by comparing solid-state analytical data of the starting materials with the corresponding analytical method collected of the cocrystal. Data from a cocrystal will be represented by an analytical response that is not simply a linear superposition of the starting materials. For example, x-ray powder diffraction ("XRPD") may be used for such comparison and the XRPD pattern of a cocrystal will differ from that of a physical mixture of the starting materials. Single crystal studies can confirm solid-state structure. In a cocrystal, the compound and the coformers each possess unique lattice positions within the unit cell of the crystal lattice. Additionally, indexing may be used to confirm the presence of a single phase.

A single crystal structure is not necessary to characterize a cocrystal. Other solid-state analytical techniques may be used to characterize cocrystals. For example, crystallographic and spectroscopic properties of cocrystals can be analyzed with XRFD, Raman spectroscopy, infrared spectroscopy, and solid-state 13C NMR spectroscopy, alone or in combination with each other, among other techniques. Cocrystals often also exhibit distinct thermal behavior compared with other forms of the corresponding compound. Thermal behavior may be analyzed by such techniques as capillary melting point, thermogravimetric analysis (TGA), and differential scanning calorimetry (DSC) to name a few. These techniques can be used to identify and characterize the cocrystals.

The entire XRPD pattern output from a diffractometer may be used to characterize a cocrystal. A smaller subset of such data, however, may also be suitable for characterizing a cocrystal. For example, a collection of one or more peaks from such a pattern may be used to characterize a cocrystal. Indeed, even a single XRPD peak may be used to characterize a cocrystal. Similarly, subsets of spectra of other techniques may be used alone or in combination with other analytical data to characterize cocrystals. In such examples of characterization as provided herein, in addition to the x-ray peak data, one also is able to provide the identity of the guest and host of the cocrystal and, often, their respective molar ratio as part of the characterization.

An XRPD pattern is an x-y graph with °2θ (diffraction angle) on the x-axis and intensity on the y-axis. These are the peaks which may be used to characterize a cocrystal. The peaks are usually represented and referred to by their position on the x-axis rather than the intensity of peaks on the y-axis because peak intensity can be particularly sensitive to sample orientation. Thus, intensity is not typically used by those skilled in the pharmaceutical arts to characterize cocrystals.

As with any data measurement, there is variability in x-ray powder diffraction data. In addition to the variability in peak intensity, there is also variability in the position of peaks on the x-axis. This variability can, however, typically be accounted for when reporting the positions of peaks for purposes of characterization. Such variability in the position of peaks along the x-axis derives from several sources. One comes from sample preparation. Samples of the same crystalline material, prepared under different conditions, may yield slightly different diffractograms. Factors such as particle size, moisture content, solvent content, and orientation may all affect how a sample diffracts x-rays. Another source of variability comes from instrument parameters. Different x-ray instruments operate using different parameters and these may lead to slightly different diffraction patterns from the same crystalline cocrystal. Likewise, different software packages process x-ray data differently and this also leads to variability. These and other sources of variability are known to those of ordinary skill in the pharmaceutical arts.

The present invention is directed to overcoming deficiencies in the art.

SUMMARY OF THE INVENTION

One aspect of the present invention relates to a cocrystal of epigallocatechin gallate and caffeine.

Another aspect of the present invention relates to a process for preparing a cocrystal of epigallocatechin gallate and caffeine. This method involves combining a 2:1 molar ratio of caffeine and EGCG under conditions effective to prepare a cocrystal of epigallocatechin gallate and caffeine.

A further aspect of the present invention relates to a composition comprising a cocrystal of the present invention and an excipient.

Another aspect of the present invention relates to a tablet or capsule comprising the cocrystal of epigallocatechin gallate and caffeine according to the present invention.

A further aspect of the present invention relates to a foodstuff comprising the cocrystal of epigallocatechin gallate and caffeine according to the present invention.

Another aspect of the present invention relates to a method of treating a subject. This method involves administering a cocrystal of epigallocatechin gallate and caffeine according to the present invention to a subject under conditions effective to treat the subject.

The present invention relates to alternative solid forms of EGCG and caffeine by cocrystallization. The resulting cocrystals were developed and evaluated for their physical properties and compared with the parent compounds.

DETAILED DESCRIPTION OF THE INVENTION

The present invention relates to cocrystals of epigallocatechin gallate and caffeine.

Epigallocatechin gallate (EGCG), also known as epigallocatechin-3-gallate, is the ester of epigallocatechin and gallic acid, and is a type of catechin. EGCG, the most abundant catechin in tea, is a polyphenol having the chemical structure

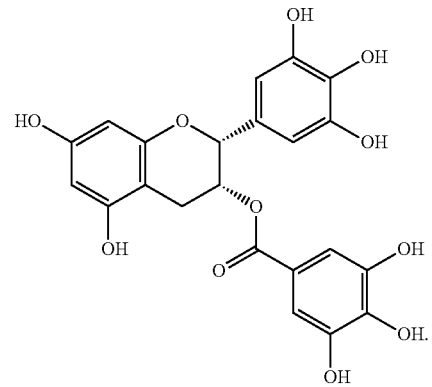 [SMILES: O=C(O[C@@H]1Cc2c(O)cc(O)cc2O[C@@H]1c1cc(O)c(O)c(O)c1)c1cc(O)c(O)c(O)c1]

Caffeine is a central nervous system (CNS) stimulant of the methylxanthine class. It is the most widely consumed psychoactive drug. There are several known mechanisms of action to explain the effects of caffeine. The most prominent is that it reversibly blocks the action of adenosine on its receptor and consequently prevents the onset of drowsiness induced by adenosine. Caffeine also stimulates certain portions of the autonomic nervous system. Caffeine is a bitter, white crystalline purine, a methylxanthine alkaloid, and is chemically related to the adenine and guanine bases of deoxyribonucleic acid (DNA) and ribonucleic acid (RNA). Caffeine has the chemical structure

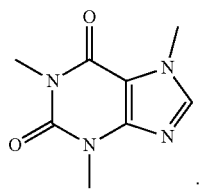

The present invention relates to an alternative solid form of EGCG and caffeine by cocrystallization. The resulting cocrystals were developed and evaluated for their physical properties and compared with the parent compounds.

In describing the cocrystals of the present invention, the following terms are defined for clarity.

By "peak" it is meant a signal that is not noise and which represents a reflection in the x-ray powder diffraction pattern. A person of ordinary skill in the art will recognize that some peaks are susceptible to preferred orientation or particle statistical affects. The fact that a peak may not be visible due to these affects does not mean the peak is not present in the material. Thus, to rule out the presence of a peak other than due to such artifacts, it may be necessary to run replicate samples of the materials analyzed.

By "form" it is meant a 2:1 cocrystal of EGCG and caffeine that can be distinguished analytically from other 2:1 cocrystals of EGCG and caffeine. Techniques such as x-ray powder diffraction and melting point may be used to distinguish such forms. Two forms of cocyrstals of EGCG and caffeine are described herein, including Form I and Form II.

A first aspect of the present invention relates to a cocrystal of epigallocatechin gallate and caffeine.

According to one embodiment, the molar ratio of caffeine to epigallocatechin gallate is about 2 to 1.

According to another embodiment, the molar ratio of caffeine to epigallocatechin gallate is 2 to 1.

According to a further embodiment, the cocyrstal of the present invention is a cocrystal of Form I.

The Form I cocrystal is a cocrystal of EGCG and caffeine.

In one embodiment, the cocrystal of the present invention is a cocrystal of Form I containing about 2 moles of caffeine, including 2 moles of caffeine for each mole of epigallocatechin gallate.

Figure 1:
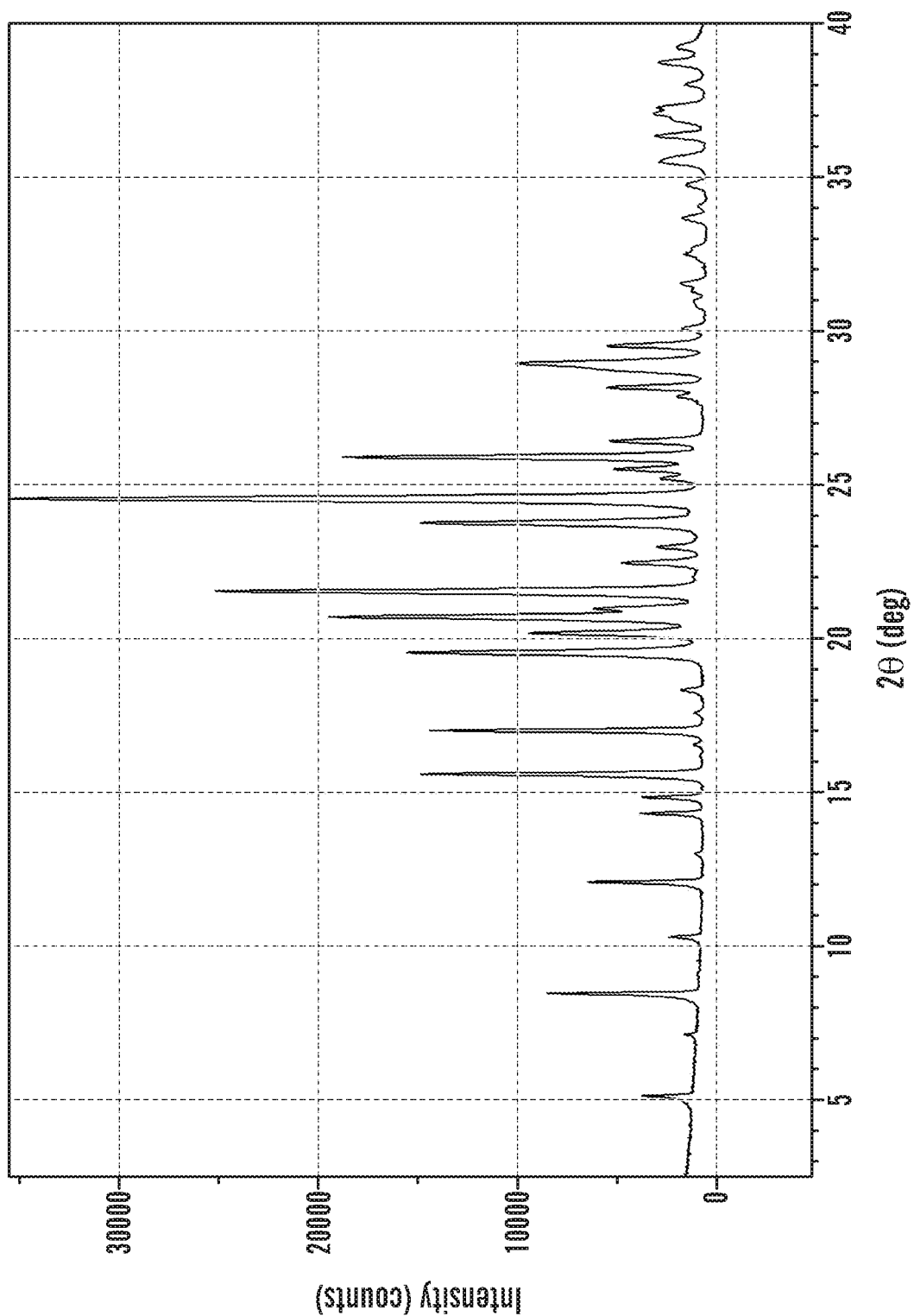
FIG. 1 is an x-ray powder diffraction pattern of epigallocatechin gallate.
Figure 2:
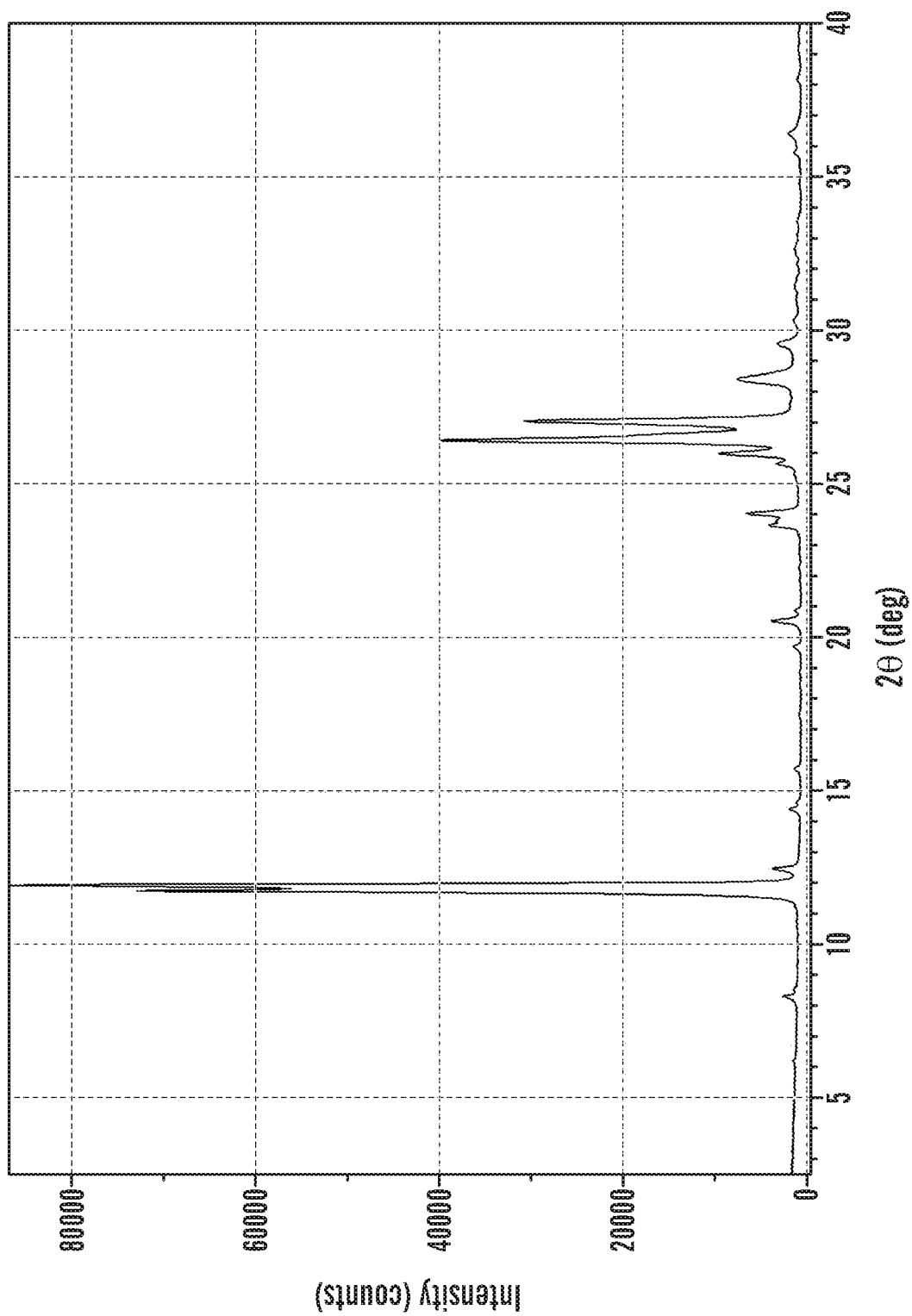
FIG. 2 is an x-ray powder diffraction pattern of caffeine.
Figure 3:
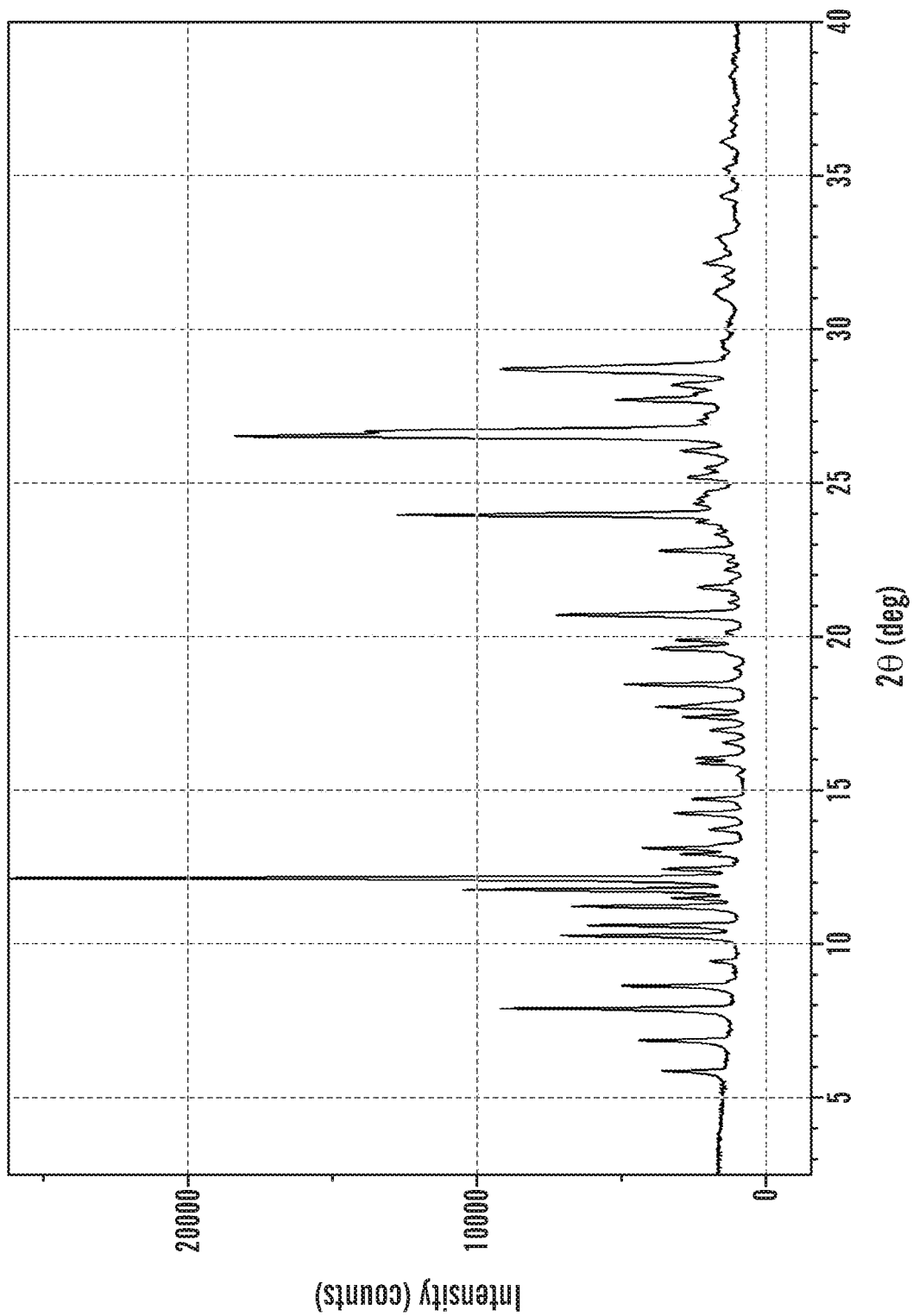
FIG. 3 is an x-ray powder diffraction pattern of a Form I cocrystal of EGCG and caffeine in a 2:1 stoichiometry of caffeine to EGCG.
Figure 4:
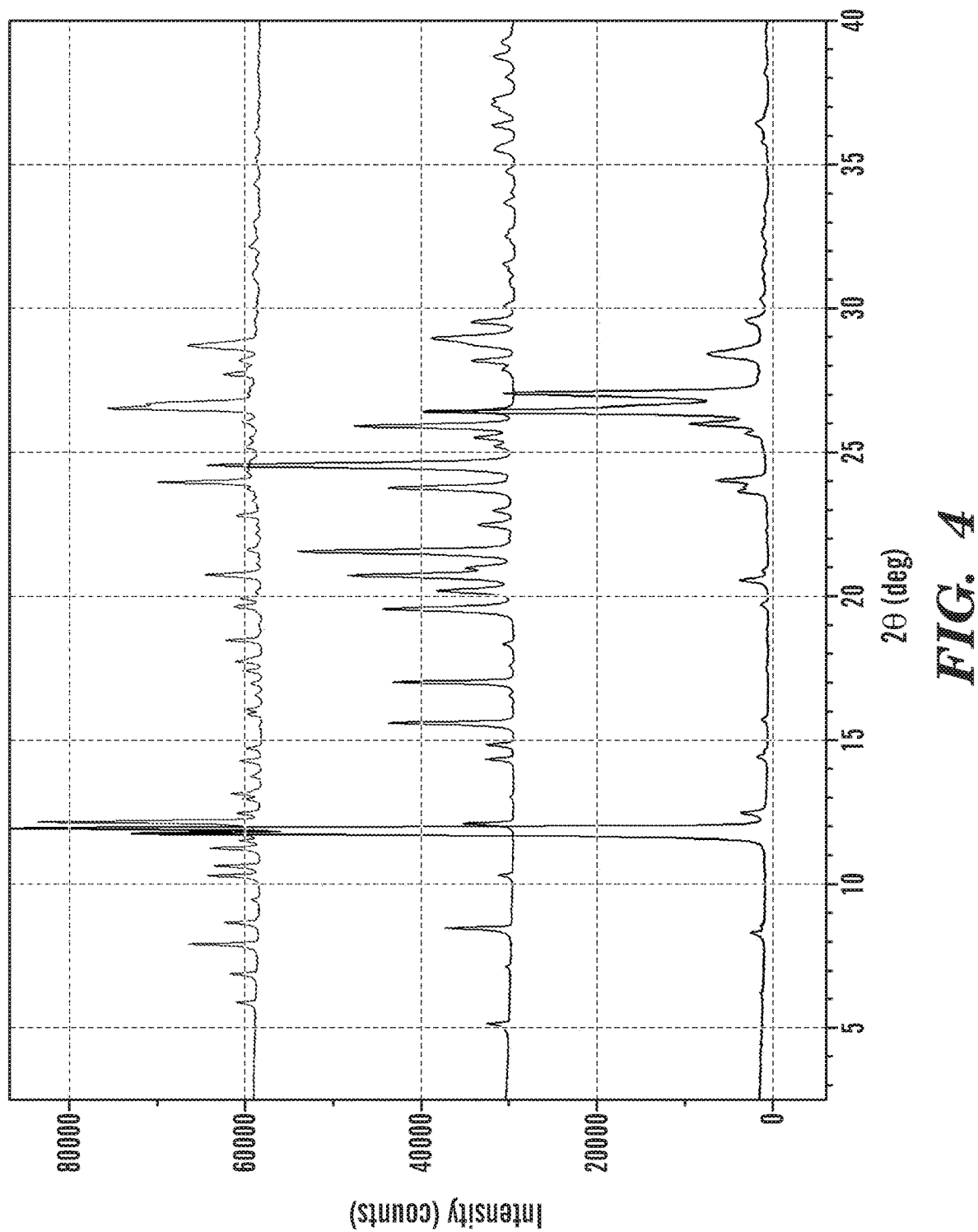
FIG. 4 is an overlay of FIGS. 1-3.
Figure 5:
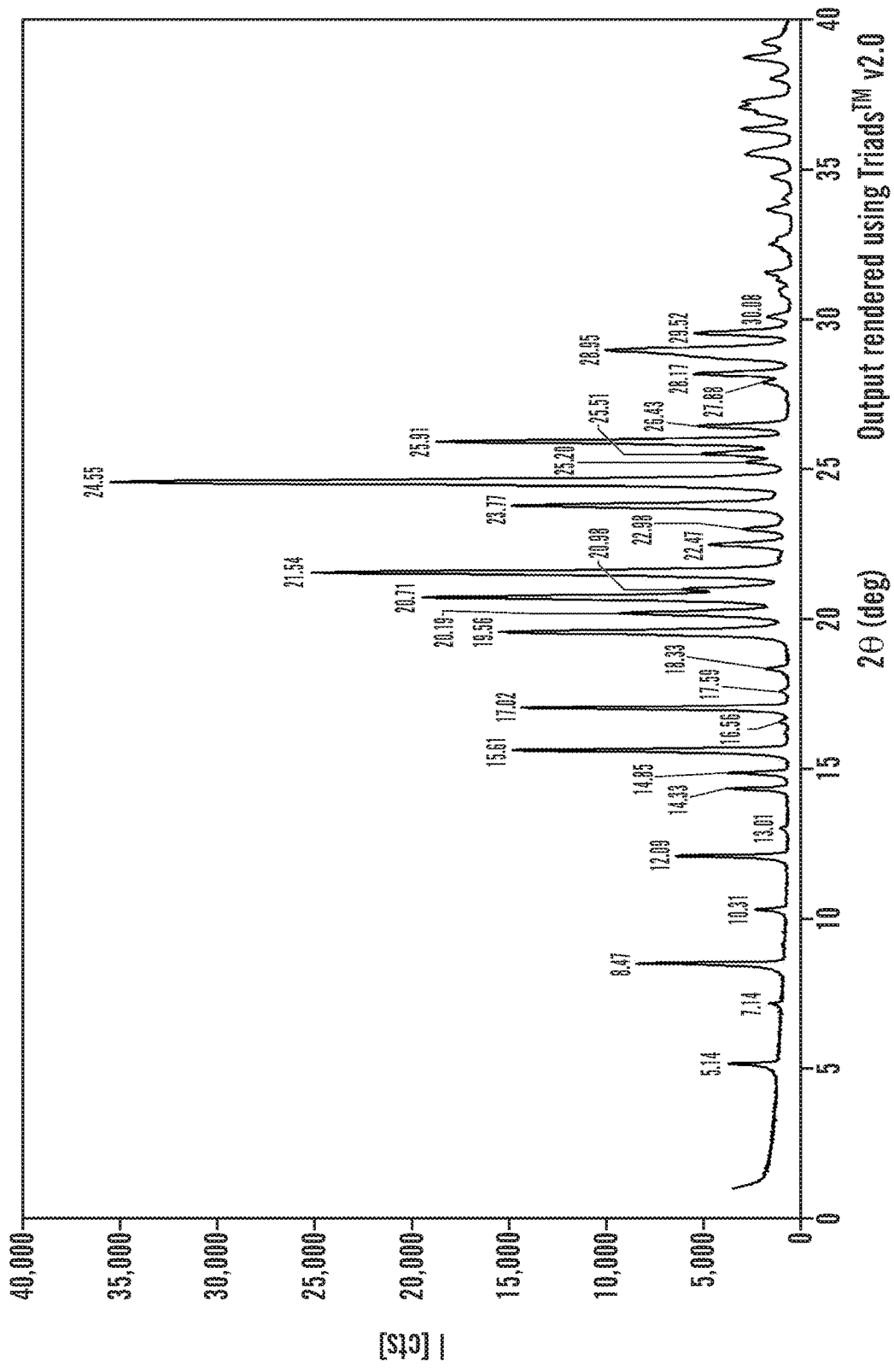
FIG. 5 is a peak picked x-ray powder diffraction pattern of epigallocatechin gallate.
Figure 6:
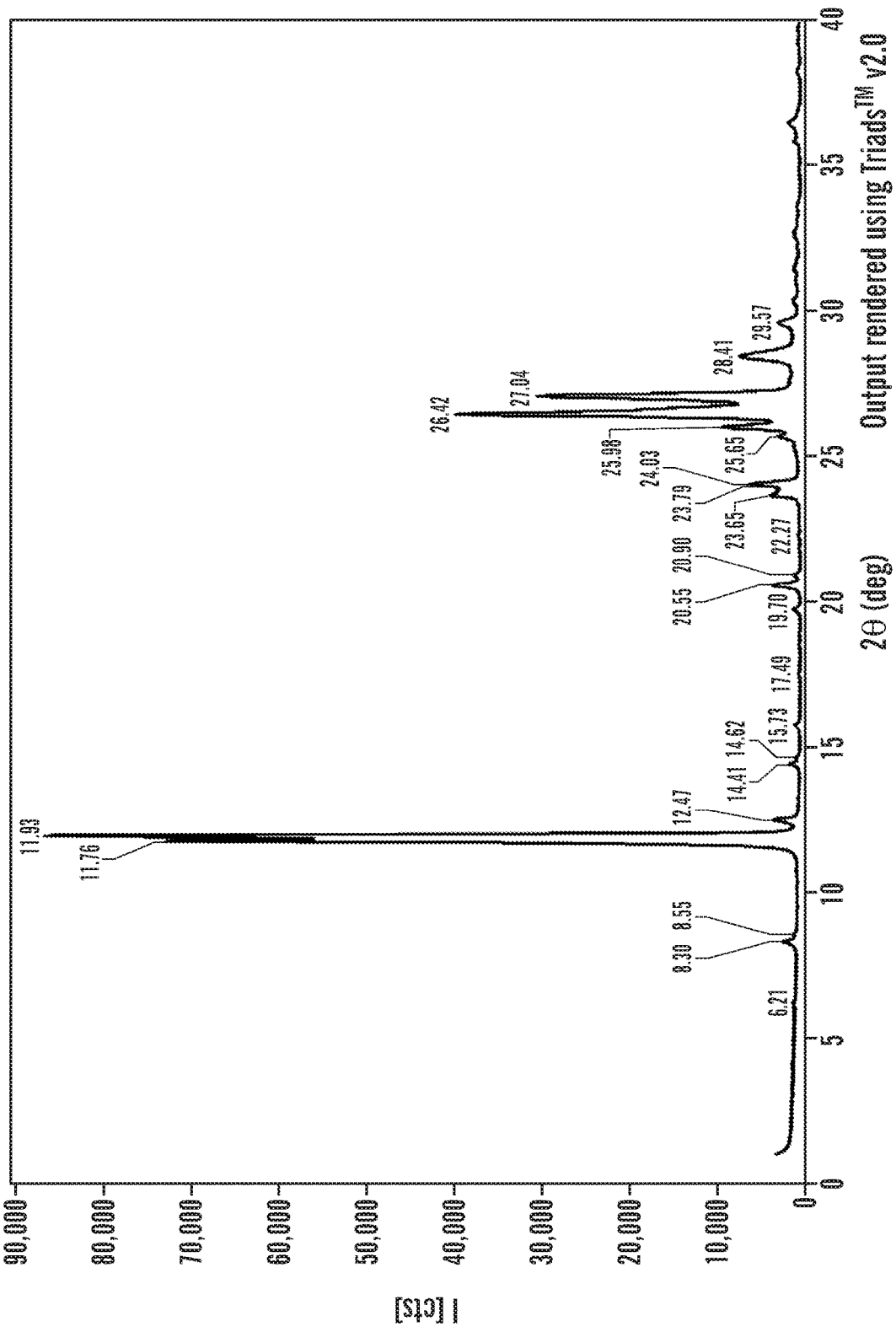
FIG. 6 is a peak picked x-ray powder diffraction pattern of caffeine.

By comparing FIGS. 1, 2, and 3 (FIGS. 5, 6, and 7 being peak-picked versions, respectively), such as by viewing the overlay patterns in FIG. 4, one can readily determine that FIG. 3 represents a cocrystal rather than a mixture of materials due to the presence of peaks present in the cocrystal not present in the components. For example, the peak at about 5.9°2θ in FIG. 3 is unique in that there is no peak at this angle in either FIG. 1 or FIG. 2.

Form I can be distinguished from Form II (discussed infra) by the peak at about 6.9°2θ in the Form I diffractogram, because there is no such peak in the diffractogram of Form II. Thus, the peaks at about 5.9°2θ and about 6.9°2θ may be used to characterize Form I.

Thus, according to one embodiment, the cocrystal is Form I having an x-ray powder diffraction pattern with peaks at about 5.9°2θ and about 6.9°2θ.

Other peaks, in addition to these peaks which may be used to characterize Form I include one or more peaks at about 7.9, 10.6, 11.3, and 16.1°2θ.

Thus, according to a further embodiment, the cocrystal is Form I having an x-ray powder diffraction pattern with peaks at about 7.9, 10.6, 11.3, or 16.1°2θ.

In some embodiments, Form I may be characterized by an x-ray powder diffraction pattern having a peak at about 5.9°2θ and 6.9°2θ and one or more peaks at about 7.9, 10.6, 11.3, or 16.1°2θ.

Due to the sources of variability discussed supra in the Background of the Invention, it is common to recite x-ray diffraction peaks using the word "about" prior to the peak value in °2θ which presents the data to within 0.1 or 0.2°2θ of the stated peak value depending on the circumstances. All x-ray powder diffraction peaks cited herein are reported with a variability on the order of 0.2°2θ and are intended to be reported with such a variability whenever disclosed herein whether the word "about" is present or not.

In one embodiment of the present invention, Form I is a 2:1 cocrystal of caffeine to epigallocatechin gallate that may be characterized by an x-ray powder diffraction pattern substantially in accordance with that of FIG. 3.

In these and other embodiments, Form I may be distinguished from other forms (e.g., Form II, discussed infra) by its melting point. Hotstage microscopy reveals that Form I melts at about 139° C., whereas Form II melts at about 147° C. Caffeine melts at about 235° C. and EGCG melts between about 218 and 221° C. Thus, the peak at about 5.9°2θ and a melting point of about 139° C. may be used to characterize Form I.

In other embodiments, the peak at about 5.9°2θ and a melting point of about 139° C. together with one or more peaks at about 6.9, 7.9, 10.6, 11.3, or 16.1°2θ may be used to characterize Form I.

Figure 7:
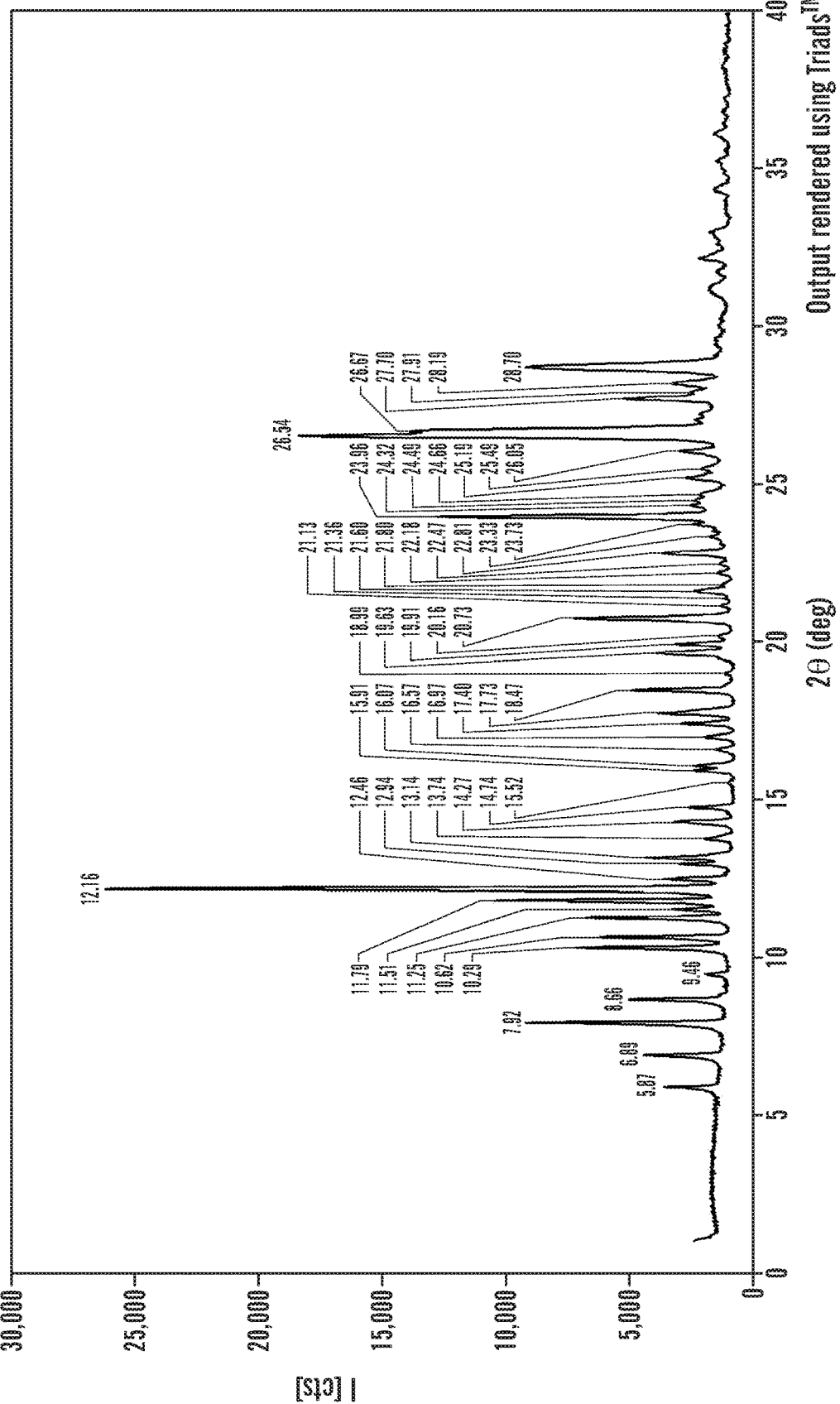
FIG. 7 is a peak picked x-ray powder diffraction pattern of a Form I cocrystal of EGCG and caffeine in a 2:1 stoichiometry of caffeine to EGCG.
Figure 8:
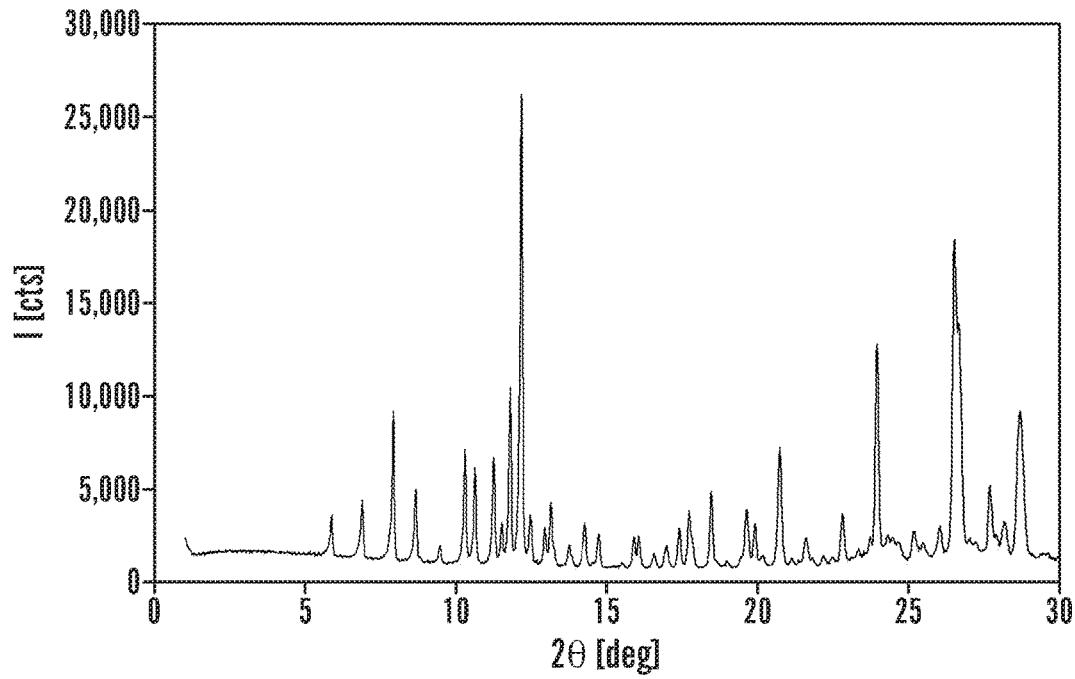
FIG. 8 is the indexing solution corresponding to the x-ray powder diffraction pattern of FIG. 3.

FIG. 8 shows the indexing solution of the x-ray powder diffraction pattern in FIGS. 3 and 7. Because there is a solution, there is additional confirmation that a cocrystal has been formed as a single phase. The solution further reveals that the unit cell is monoclinic. Thus, two angles of the unit cell are 90°. The third angle has been found to be 97.85°. The unit cell volume is about 5050 cubic Angstroms (to within 1%). These data, as well other data reported in FIG. 8, may be used to characterize a 2:1 cocrystal of caffeine to epigallocatechin gallate. The indexing solution data may be used alone or in connection with peaks in the x-ray powder diffraction pattern to characterize Form I.

For example, in some embodiments, the Form I cocrystal of caffeine to epigallocatechin gallate may be characterized by a peak at about 6.9°2θ, where the unit cell has a volume of about 5050 cubic Angstroms.

According to another embodiment, the cocyrstal of the present invention is a cocrystal of Form II.

The Form II cocrystal is a cocrystal of EGCG and caffeine.

In one embodiment, the cocrystal of the present invention is a cocrystal of Form II containing about 2 moles of caffeine, including 2 moles of caffeine for each mole of epigallocatechin gallate.

Figure 11:
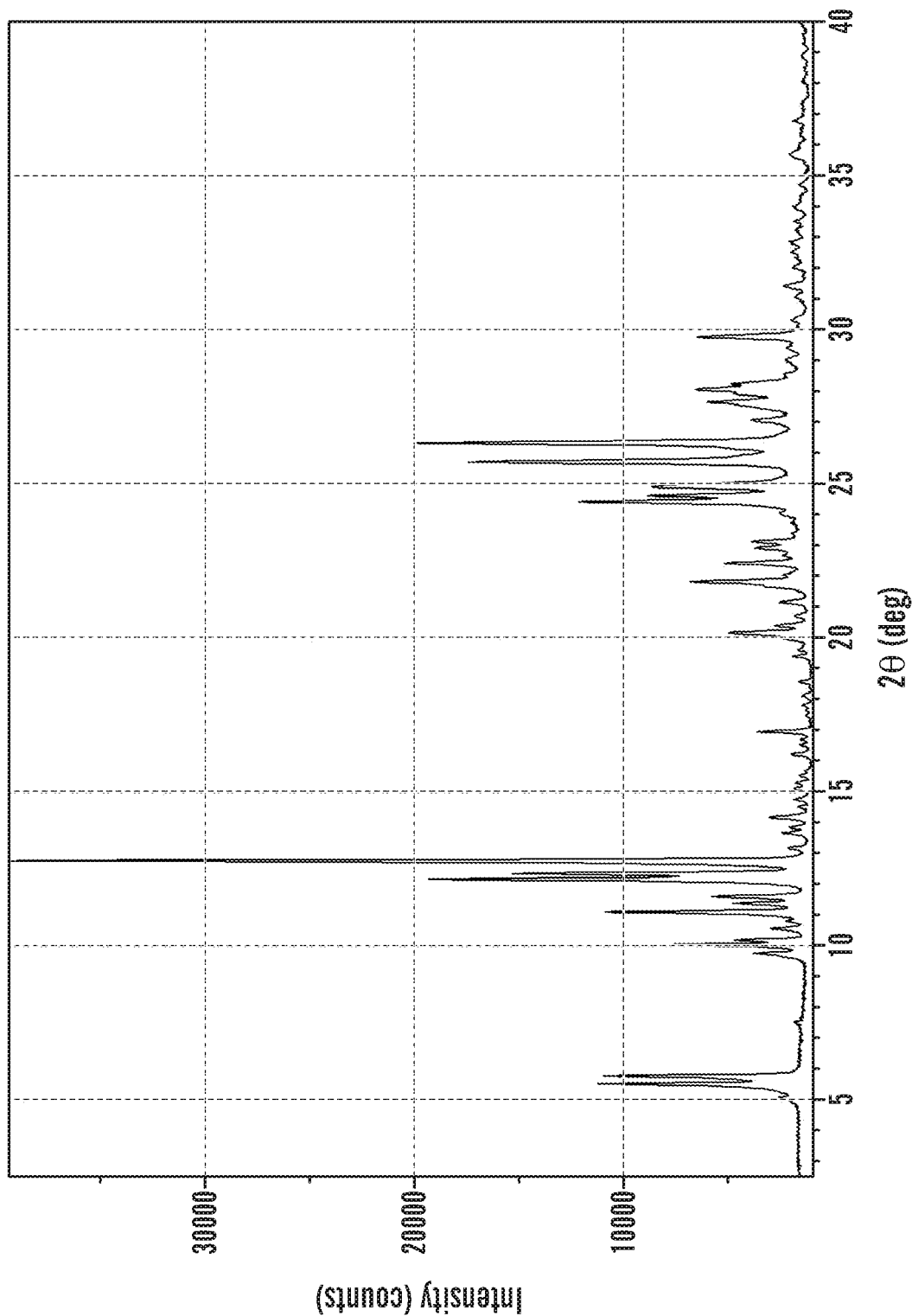
FIG. 11 is an x-ray powder diffraction pattern of Form II of a cocrystal of EGCG and caffeine in a 2:1 stoichiometry of caffeine to EGCG.

In one embodiment, the Form II cocrystal of caffeine to epigallocatechin gallate may be characterized by an x-ray powder diffraction pattern substantially in accordance with that of FIG. 11.

Figure 12:
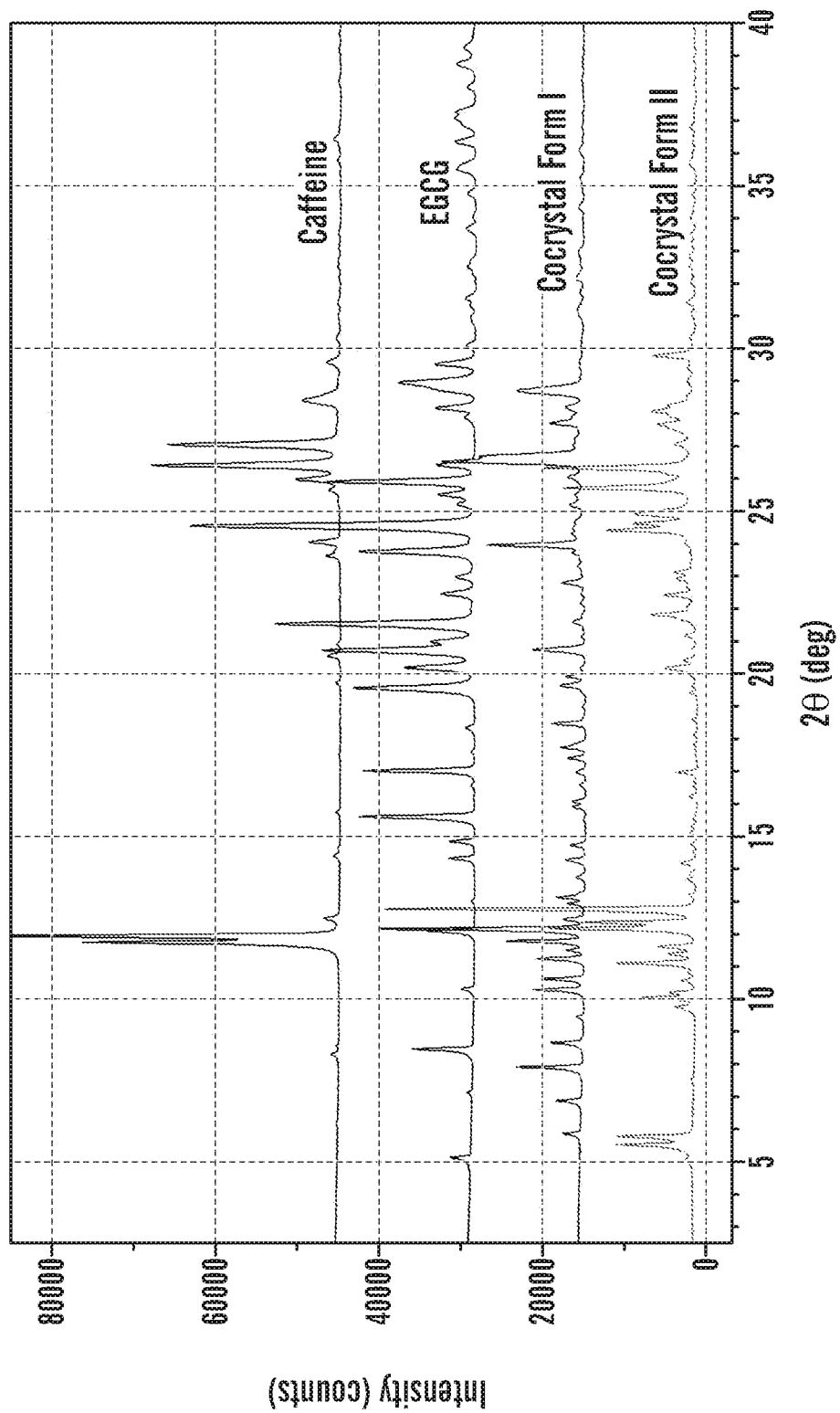
FIG. 12 is an overlay of Forms I and II of EGCG:caffeine cocrystals, caffeine and EGCG.

By comparing FIGS. 1, 2, and 11 (FIGS. 5, 6, and 13 being peak-picked versions respectively), such as by viewing the overlay patterns in FIG. 12, one can readily determine that FIG. 11 represents a cocrystal rather than a mixture of materials due to the presence of peaks present in the cocrystal not present in the components. For example, Form II has two peaks in close proximity to each other at about 5.5 and 5.8°2θ. The closest such peaks in EGCG are at about 5.1 and 7.1°2θ. In caffeine, the closest such peaks are at about 6.2 and 8.3°2θ. In Form I, the closest two peaks are at about 5.9 and 6.9°2θ. Thus, considering a variability of 0.2°2θ, only Form II has two peaks between about 5.5 and 5.8°2θ and can therefore be characterized by two peaks between about 5.5 and about 5.8°2θ. Accordingly, having two peaks between 5.3 and 6.0°2θ is characteristic of Form II.

Thus, according to one embodiment, the cocrystal is Form II having an x-ray diffraction pattern with two peaks between about 5.5 and 5.8°2θ.

A melting point of about 148° C. may further be used to characterize Form II with or without two peaks between about 5.3 and 6.0°2θ.

In some embodiments, Form II may be characterized by an x-ray powder diffraction pattern having two peaks between about 5.5 and 5.8°2θ and one or more peaks at about 12.2, 12.4, or 12.8°2θ and, optionally, a melting point of about 148° C.

Figure 13:
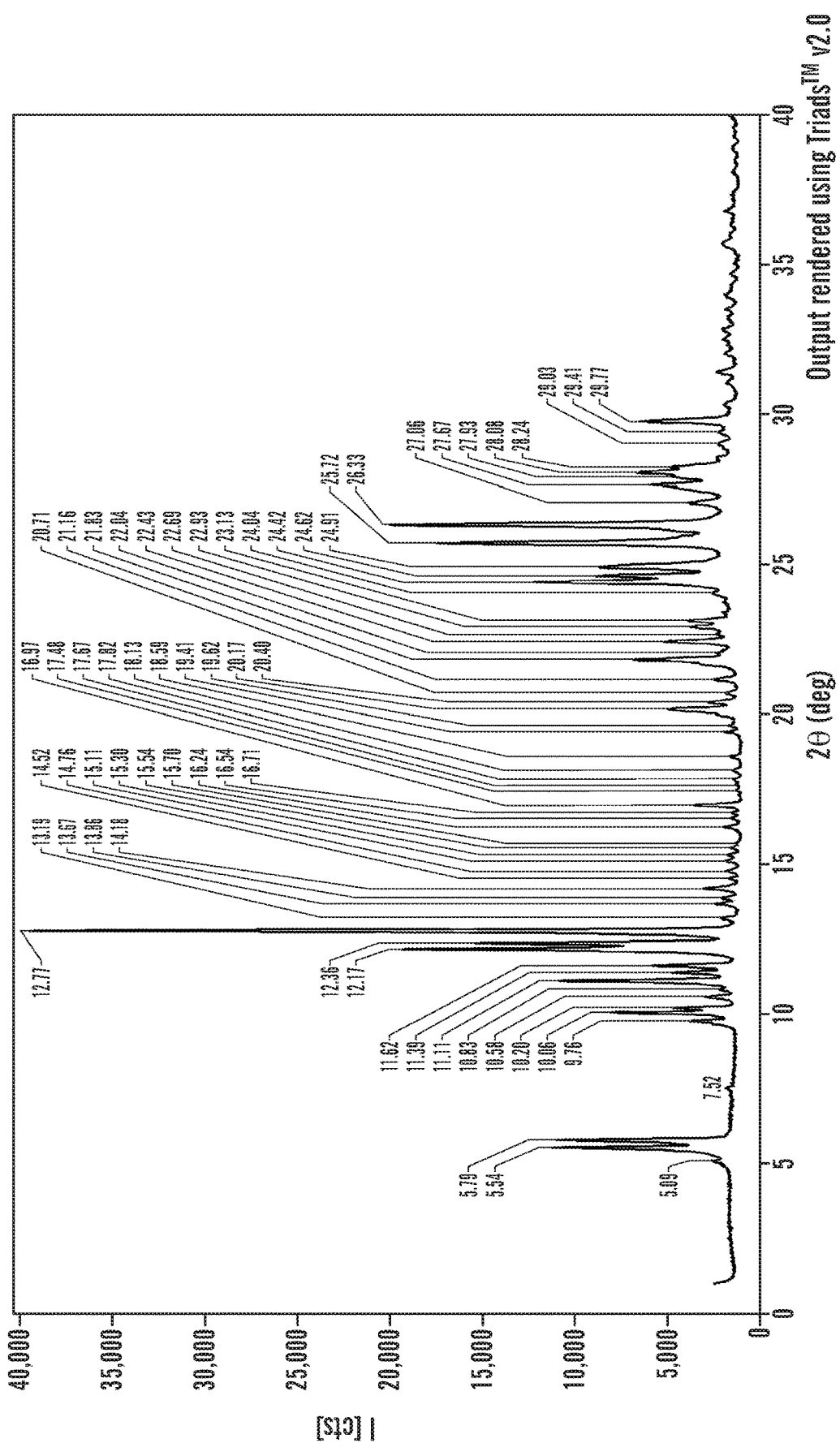
FIG. 13 is FIG. 11 peak-picked.
Figure 14:
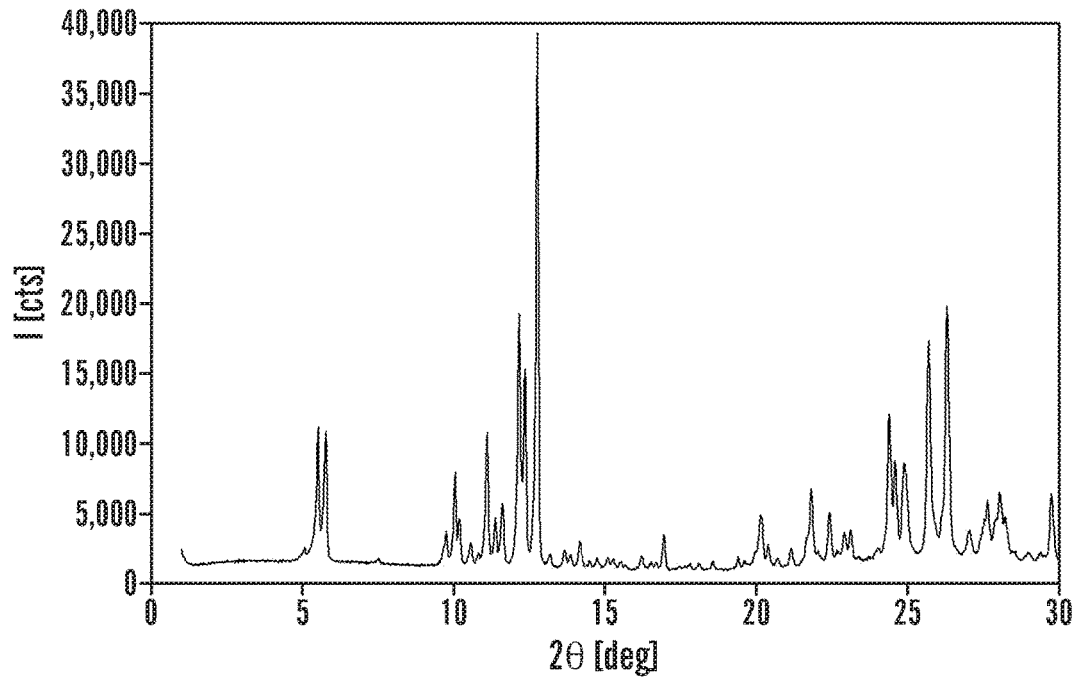
FIG. 14 is the indexing solution corresponding to the x-ray powder diffraction pattern of FIG. 11.

FIG. 14 shows the indexing solution of the x-ray powder diffraction pattern in FIGS. 11 and 13. Because there is a solution, there is additional confirmation that a cocrystal has been formed as a single phase. The solution further reveals that the unit cell is monoclinic. Thus, two angles of the unit cell are 90°. The third angle has been found to be 91.44°. The unit cell volume is about 5040 cubic Angstroms (to within 1%). These data, as well other data reported in FIG. 14, may be used to characterize Form II of a 2:1 cocrystal of caffeine to epigallocatechin gallate. The indexing solution data may be used alone or in connection with peaks in the x-ray powder diffraction pattern to characterize a 2:1 cocrystal of caffeine to epigallocatechin gallate.

For example, in some embodiments, Form II of 2:1 cocrystals of caffeine to epigallocatechin gallate may be characterized by two peaks between about 5.5 and about 5.8°2θ, where the unit cell has a volume of about 5040 cubic Angstroms.

Another aspect of the present invention relates to a process for preparing a cocrystal of epigallocatechin gallate and caffeine. This method involves combining a 2:1 molar ratio of caffeine and EGCG under conditions effective to prepare a cocrystal of epigallocatechin gallate and caffeine.

In one embodiment, suitable conditions for carrying out this method include, without limitation, combining in water a 2:1 molar ratio of caffeine and EGCG and subjecting the combination to vacuum filtration to prepare crystals of epigallocatechin gallate and caffeine.

In another embodiment, suitable conditions include, without limitation, combining in water a 2:1 molar ratio of caffeine and EGCG and subjecting the combination to centrifugation to isolate crystals of epigallocatechin gallate and caffeine.

Cocrystals of the present invention, such as Form I or Form II, may be made, according to one embodiment, by slurry-titration methods.

In many embodiments, a 1:2 molar ratio of caffeine and EGCG may be slurried in water followed by vacuum filtration to afford cocrystals of caffeine and EGCG. Such processes may produce Form I or Form II. Form II may be the form obtained upon scaling up the reaction conditions.

A further aspect of the present invention relates to a composition comprising a cocrystal of the present invention and an excipient.

According to one embodiment, the composition includes Form I cocrystals of caffeine to epigallocatechin gallate, e.g., characterized by an x-ray powder diffraction pattern substantially in accordance with that of FIG. 3 or any other characterizing features described herein.

According to another embodiment, the composition includes Form II cocrystals of caffeine to epigallocatechin gallate, e.g., characterized by an x-ray powder diffraction pattern substantially in accordance with that of FIG. 11 or any other characterizing features described herein.

According to a further embodiment, the composition includes both Form I and Form II cocrystals of caffeine to epigallocatechin gallate as described herein.

According to yet another embodiment, the composition includes either Form I cocrystal or Form II cocrystal, but not both Form I and Form II cocrystals.

The composition of the present invention can be utilized to achieve a desired pharmacological or dietary effect by administration to a patient.

In one embodiment, composition of the present invention may be administered to a subject in need of a desired pharmacological or dietary effect.

In another embodiment, composition of the present invention may be administered to a subject where a particular need has not been identified other than general wellbeing.

Suitable excipients for use in the composition of the present invention include, without limitation, any excipient which is relatively non-toxic and innocuous to a patient at concentrations consistent with effective activity of the cocrystal of the invention so that any side effects ascribable to the excipients do not vitiate the beneficial effects of the cocrystal. Such excipients include, without limitation, solvents, diluents, or other liquid vehicles, dispersion or suspension aids, surface active agents, isotonic agents, thickening or emulsifying agents, preservatives, solid binders, lubricants, adjuvants, vehicles, delivery systems, disintegrants, absorbents, preservatives, surfactants, colorants, flavorants, or sweeteners and the like, as suited to the particular dosage form desired.

The amount of compound that may be included in a composition of the present invention is that amount which produces a result or exerts an influence on the particular individual receiving the composition. Cocrystals of the present invention can be administered with, e.g., pharmaceutically-acceptable excipients well known in the art using any effective conventional dosage unit forms, including immediate, slow and timed release preparations, orally, parenterally, topically, nasally, ophthalmically, optically, sublingually, rectally, vaginally, and the like.

The composition may be used alone or in combination with other compositions to improve animal or human health or nutrition.

Another aspect of the present invention relates to a tablet or capsule comprising the cocrystal of epigallocatechin gallate and caffeine according to the present invention.

The cocrystal of epigallocatechin gallate and caffeine according to the present invention is suitable as a dietary supplement, or a component in a dietary supplement.

In one embodiment, the cocrystal or composition thereof is incorporated into a capsule.

In another embodiment, the cocrystal or composition thereof is incorporated into a compressed tablet.

In yet another embodiment, the cocrystal or co-crystal containing composition is added to a foodstuff. The cocrystal may be added to any foodstuff, including, without limitation coffee, tea, soda, fruit drink, water, sauce, candy, cereal, bread, fruit mixes, fruit salads, salads, snack bars, fruit leather, health bars, granola, smoothies, soups, juices, cakes, pies, shakes, ice cream, health drinks.

A further aspect of the present invention relates to a foodstuff comprising the cocrystal of epigallocatechin gallate and caffeine according to the present invention.

Another aspect of the present invention relates to a method of treating a subject. This method involves administering a cocrystal of epigallocatechin gallate and caffeine according to the present invention to a subject under conditions effective to treat the subject.

EGCG can be used for prevention or therapy of various diseases, based on its antioxidant effects. It is useful for treatment or prevention of diseases including, but not limited to neurodegenerative diseases or conditions, such as Alzheimer's disease; upper respiratory diseases, including those caused by an infection; dementia, such as AIDS-dementia; oncological disorders, such as cancer; inflammatory or auto-immune diseases, such as rheumatoid arthritis or diabetic neuropathies; or a disease or condition caused by an infection by virus or bacteria.

The cocrystal or composition containing the cocrystal of the present invention may be administered in a single unit dosage form that contains an amount of cocrystal effective to treat a subject. The cocrystal or composition containing the cocrystal can also include suitable excipients or stabilizers, and can be in solid or liquid form such as, tablets, capsules, powders, solutions, suspensions, or emulsions. Typically, the composition will contain from about 0.01 to 99% w/w, or from about 5 to 95% w/w cocrystal.

The cocrystal, when combined with any suitable excipients or stabilizers, and whether administered alone or in the form of a composition, can be administered orally. For most therapeutic purposes, the cocrystal can be administered orally as a solid or as a solution or suspension in liquid form.

The solid unit dosage forms of the cocrystal can be of a conventional type. The solid form can be a capsule, such as an ordinary gelatin type containing the cocrystal and a carrier, for example, lubricants and inert fillers such as, lactose, sucrose, or cornstarch. In another embodiment, the cocrystal is tableted with conventional tablet bases such as lactose, sucrose, or cornstarch in combination with binders like acacia or gelatin, disintegrating agents such as cornstarch, potato starch, or alginic acid, and a lubricant such as stearic acid or magnesium stearate.

The cocrystal may be administered in combination with other therapeutic regimens that are known in the art, whether now known or hereafter developed.

EXAMPLES

The following examples are provided to illustrate embodiments of the present invention but they are by no means intended to limit its scope.

Example 1—Materials and Methods

All chemicals were obtained from commercial sources and used without further purification. Attempts to generate cocrystals were made using multiple solvent based techniques. X-ray powder diffraction was used as a primary technique for identification of the EGCG-caffeine cocrystal. The stoichiometric ratio of each component in the cocrystal was determined by proton solution nuclear magnetic resonance spectroscopy.

XRPD patterns were collected with a PANalytical X'Pert PRO MPD diffractometer using an incident beam of Cu radiation produced using an Optix long, fine-focus source. An elliptically graded multilayer mirror was used to focus Cu Kα X-rays through the specimen and onto the detector. Prior to the analysis, a silicon specimen (NIST SRM 640d) was analyzed to verify that the observed position of the Si 111 peak was consistent with the NIST-certified position. A specimen of the sample was sandwiched between 3 μm thick films and analyzed in transmission geometry. A beam-stop, short antiscatter extension, antiscatter knife edge were used to minimize the background generated by air. Soller slits for the incident and diffracted beams were used to minimize broadening from axial divergence. Diffraction patterns were collected using a scanning position-sensitive detector (X'Celerator) located 240 mm from the specimen and Data Collector software v. 2.2b.

Moisture sorption/desorption data were collected on a VTI SGA-100 Vapor Sorption Analyzer. NaCl (NIST SRM 919b) and PVP were used as calibration standards. The sample was not dried prior to analysis. Sorption and desorption data were collected over a range from 5% to 95% relative humidity ("RH") at 10% RH increments under a nitrogen purge. The equilibrium criterion used for analysis was less than 0.01% weight change in 5 minutes with a maximum equilibration time of 3 hours. Data were not corrected for the initial moisture content of the samples.

The XRPD pattern of a 2:1 molar ratio of caffeine to epigallocatechin gallate cocrystal for both Form I and Form II was indexed using proprietary SSCI software known as TRIADS™ and the methodology for the indexing is described in U.S. Pat. No. 8,576,985, which is hereby incorporated by reference in its entirety. The resulting indexed pattern is illustrated in FIGS. 8 and 14 and is based on the data set forth in FIGS. 7 and 11, respectively. Agreement between the allowed peak positions and the observed peaks indicates a consistent unit cell determination. Successful indexing of the pattern indicates that the sample is composed primarily of a single crystalline phase. Space groups consistent with the assigned extinction symbol, unit cell parameters, and derived quantities are tabulated below the figure.

Coulometric Karl Fischer ("KF") analysis for water determination was performed using a Mettler Toledo DL39 KF titrator. A blank titration was carried out prior to analysis. The sample was prepared under a dry nitrogen atmosphere, where ~1 g of the sample was dissolved in approximately 1 mL Fluka Hydranal—Coulomat AD in a pre-dried vial. The entire solution was added to the KF coulometer through a septum and mixed for 10 seconds. The sample was then titrated by means of a generator electrode, which produces iodine by electrochemical oxidation: $2\ I^- \rightarrow I_2 + 2e^-$. Two replicates were obtained to ensure reproducibility. Karl Fischer measurements on Form II revealed 13% water corresponding to about 7 moles of water.

IR spectra (FIGS. 17, 23, 25, 27, and 29) were acquired on Nicolet 6700® Fourier transform infrared (FT-IR) spectrophotometer (Thermo Scientific) equipped with an Ever-Glo mid/far IR source, potassium bromide (KBr) beamsplitter, and a deuterated triglycine sulfate (DTGS) detector. Wavelength verification was performed using NIST SRM 1921b (polystyrene). An attenuated total reflectance (ATR) accessory (Thunderdome™, Thermo Spectra-Tech), with a germanium (Ge) crystal was used for data acquisition. Each spectrum represents 256 co-added scans collected at a spectral resolution of 4 cm$^{-1}$. A background data set was acquired with a clean Ge crystal. A Log 1/R (R=reflectance) spectrum was obtained by taking a ratio of these two data sets against each other. Spectrum was analyzed using OMNIC software v7.2.

Raman spectra (FIGS. 18, 24, 26, 28, and 30) were acquired on a FT-Raman module interfaced to a Nexus 670 FT-IR spectrophotometer (Thermo Nicolet) equipped with an InGaAs detector. Wavelength verification was performed using sulfur and cyclohexane. Each sample was prepared for analysis by placing the sample in a pellet holder. Approximately 0.5 W of Nd:YVO$_4$ laser power (1064 nm excitation wavelength) was used to irradiate the sample. Each spectrum represents 256 co-added scans collected at a spectral resolution of 4 cm$^{-1}$. Spectrum was analyzed using OMNIC software v7.2.

Hot stage microscopy was performed using a Linkman hot stage (model FTIR 600) with a TMS93 controller on a Leica DM LP microscope equipped with a spot Insight color camera for acquiring images. Sample was placed on a coverslip and observed using a 20×0.40 N.A. long working distance objective with a lambda plate with crossed polars and a first order red compensator. Images were acquired using Spot Advanced software version 4.5.9.

HPLC data were collected using an Agilent 1100 series equipped with a reverse phase column (Waters, Symmetry Shield RP18, 3.5 μm, 4.6*150 mm). A gradient method with water containing 0.1% TFA and 5% ACN as mobile phase A, and ACN with 0.1% TFA as mobile phase B was run at a flow rate of 0.8 mL/min. A detector wavelength of 280 nm was used. The injection volume was 15 μL. Autosampler temp was 5° C. The following gradient was used:

| Time (min) | % mobile phase A | % mobile phase B |
|---|---|---|
| 0.00 | 100.0 | 0.00 |
| 1.20 | 100.0 | 0.00 |
| 15.50 | 71.5 | 28.5 |
| 17.00 | 71.5 | 28.5 |
| 17.10 | 100.0 | 0.00 |
| 25.00 | 100.0 | 0.00 |

Example 2—Form I Preparation

Figure 9:
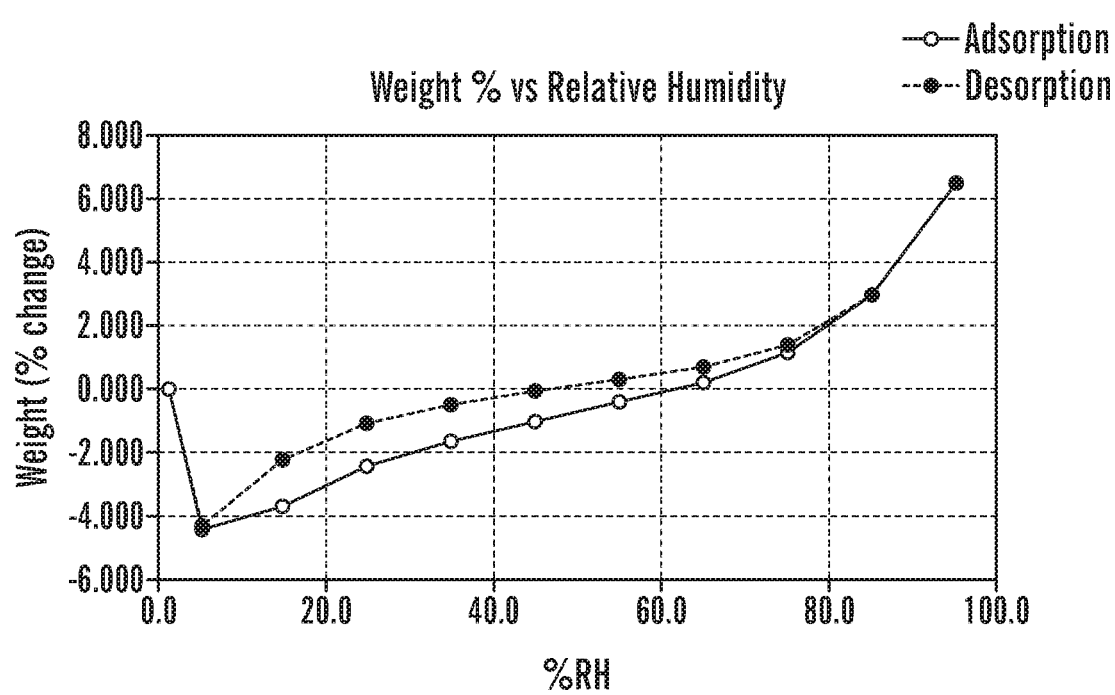
FIG. 9 is a Dynamic Vapor Sorption ("DVS") plot of a Form I cocrystal of EGCG and caffeine in a 2:1 stoichiometry (caffeine to EGCG).
Figure 10:
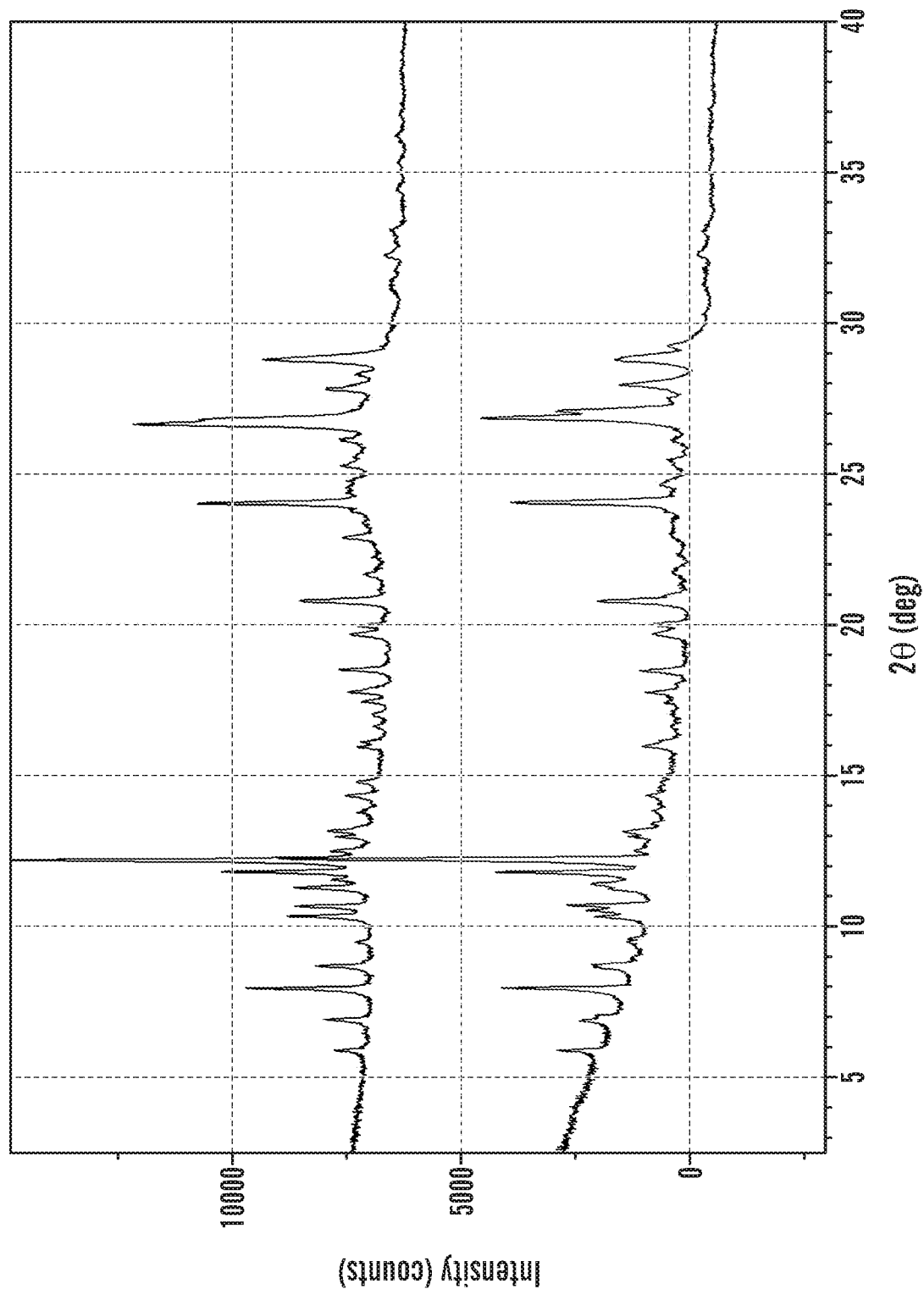
FIG. 10 is an x-ray powder diffraction pattern of the cocrystal of FIG. 9 before and after the DVS experiment.

Caffeine was received from Sigma-Aldrich (ReagentPlus/Pharmagrade), and -(-) Epigallocatechin Gallate (98.5%) was obtained from VWR. HPLC grade water was used for the slurry. Slurry cocrystallization was used for the cocrystal preparation. A stoichiometric amount (~2:1 caffeine/EGCG)) of caffeine (17.00 mg) and EGCG (16.49 mg) were suspended in water (0.4 mL). The sample was stirred at room temperature (~300 rpm) for 4 days in a capped vial protected from light. After 4 days, solids were collected by centrifuge filtration (~15 min) through 0.45 μm nylon filters. Solids were air dried for ~4 hours. FIGS. 3 and 7 are x-ray powder diffraction patterns of the resulting 2:1 cocrystal of caffeine to epigallocatechin gallate. The pattern also appears in FIG. 4 as the top diffraction pattern. A DVS study, shown in FIG. 9, showed a reversible weight gain of ~10.9% from 5 to 95% RH. Weight loss of about 10.8% was observed from 95 to 5% RH. The DVS experiment further shows that the cocrystal does not retain significant water. FIG. 10 shows a comparison of x-ray patterns before and after the DVS measurements and indicates that the cocrystal did not change during the measurements. 1H NMR spectra were further collected, which confirm a 2:1 ratio of caffeine to epigallocatechin gallate.

Example 3—Form II Preparation

Caffeine was received from Sigma-Aldrich (ReagentPlus/Pharmagrade), -(-) Epigallocatechin Gallate (>99%) was obtained from Apex Bio. HPLC grade water was used for the slurry. Slurry cocrystallization was used for the cocrystal preparation.

In Preparation one of Form II, a stoichiometric amount (~2:1 caffeine/EGCG) of caffeine (524.84 mg) and EGCG (618.84 mg) were stirred in water (2.00 mL). Thick agglomerate was observed after one day of stirring (~100 rpm, protected from light). Additional water (2.00 mL) was added and sample continued to stir. After three days of stirring, solids from the sample were recovered by vacuum filtration (~15 min). Solids were air dried for ~4 hours.

In preparation two of Form II, a stoichiometric amount (~2:1 caffeine/EGCG) of caffeine (303.05 mg) and EGCG (356.99 mg) were stirred in water (3.00 mL). The sample was stirred (~500 rpm) and protected from light for 4 days. Agglomerates were observed in the sample on day 4. Agglomerates were broken with a spatula and stirring of the sample continued. After 7 days of stirring, agglomerates were seen in the sample. Agglomerates were broken with a spatula and the sample was vacuum filtered to collect the solids. Solids were air-dried for ~4 hours.

In preparation three, a stoichiometric amount (~2:1 caffeine/EGCG) of caffeine (45.65 mg) and EGCG (41.32 mg) were stirred in water (1.00 mL). The sample was stirred (~300 rpm) and protected from light for three days. After three days, solids were recovered by centrifuging the sample (~15000 rpm for 10 minutes) through 0.45 μm nylon centrifuge tubes. Solids were allowed to air-dry overnight at ambient in open vials (covered with pin-holed aluminum paper) protected from light.

Example 4—Dissolution Study

Duplicate samples were prepared by adding about 400 mg of Form II to 5 mL phosphate buffer (pH 6.8) and stirred on a shaker block (~250 rpm). At time points corresponding to 1, 3, 5, 10, 15, 30, 45, 60 min, and 24 hours, 0.4 mL sample was withdrawn from each sample, diluted as required, and analyzed for concentration by HPLC. Average concentration for each time point was determined from the duplicate samples.

Figure 19:
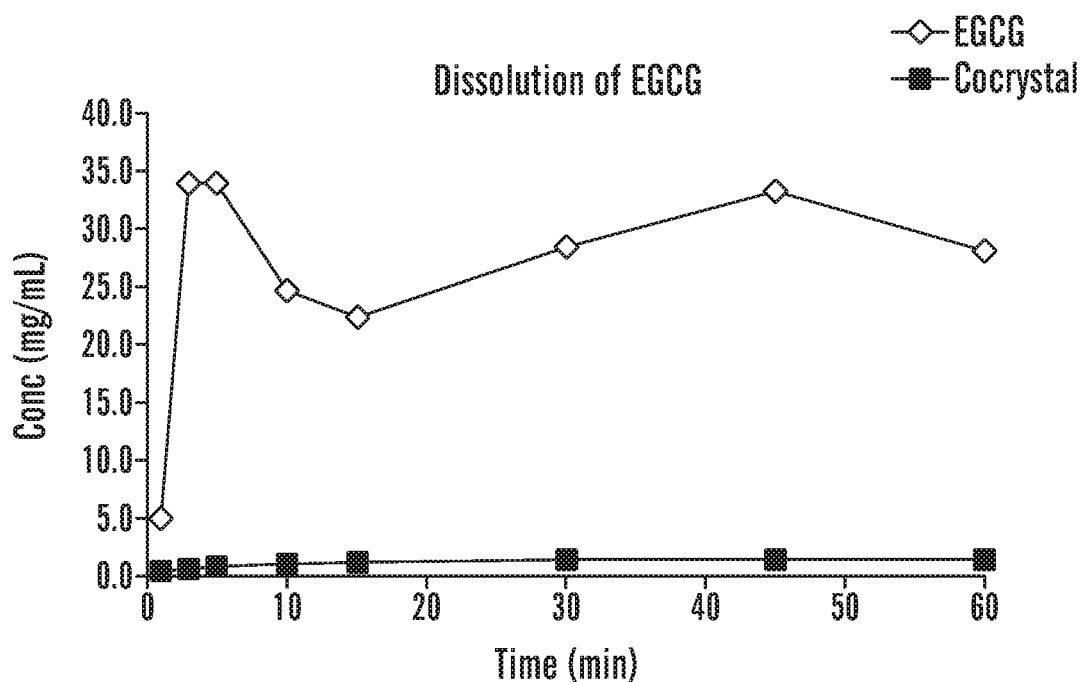
FIG. 19 is a dissolution profile comparing Form II EGCG:caffeine to EGCG alone.
Figure 20:
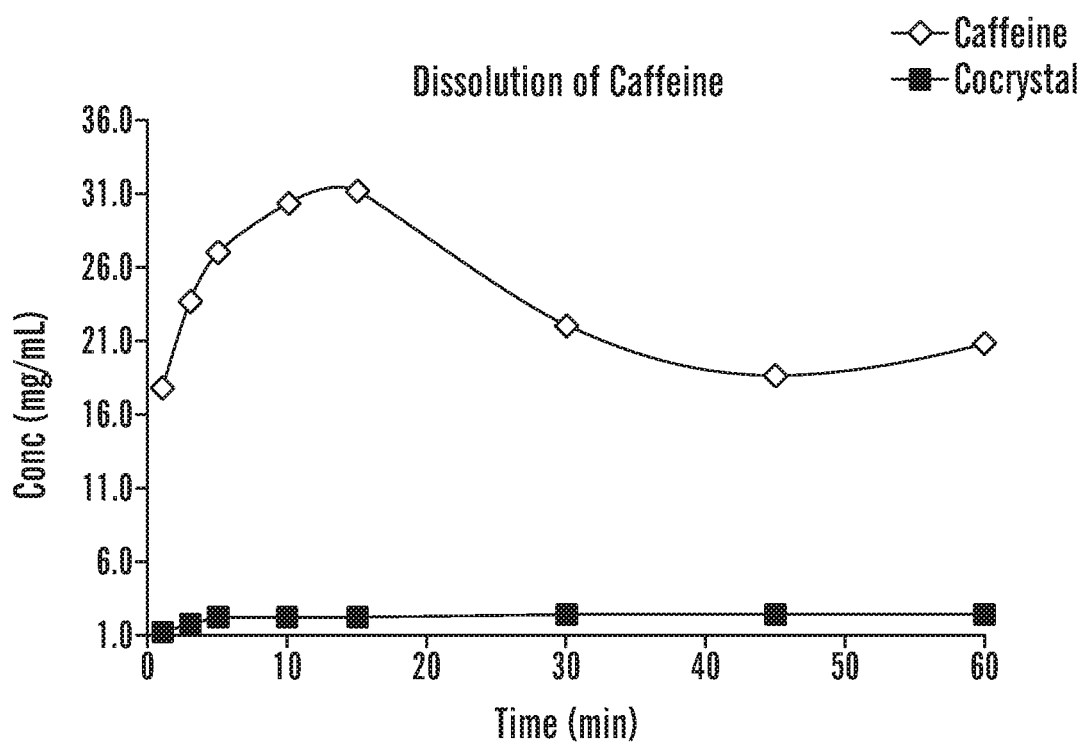
FIG. 20 is a dissolution profile comparing Form II EGCG:caffeine to caffeine alone.

FIGS. 19 and 20 are dissolution profiles for Form II (preparation one) with respect to EGCG and caffeine alone. The solubility of EGCG and caffeine alone as well as from Form II was measured from pH 6.8 Phosphate buffer and is reported in Table 1.

TABLE 1

| Compound | Solubility after 24 hours in pH 6.8 phosphate buffer |
|---|---|
| EGCG | 24 mg/mL |
| EGCG from cocrystal Form II | 0.6 mg/mL |
| Caffeine | 18 mg/mL |
| Caffeine from cocrystal Form II | 2.3 mg/mL |

Figure 21:
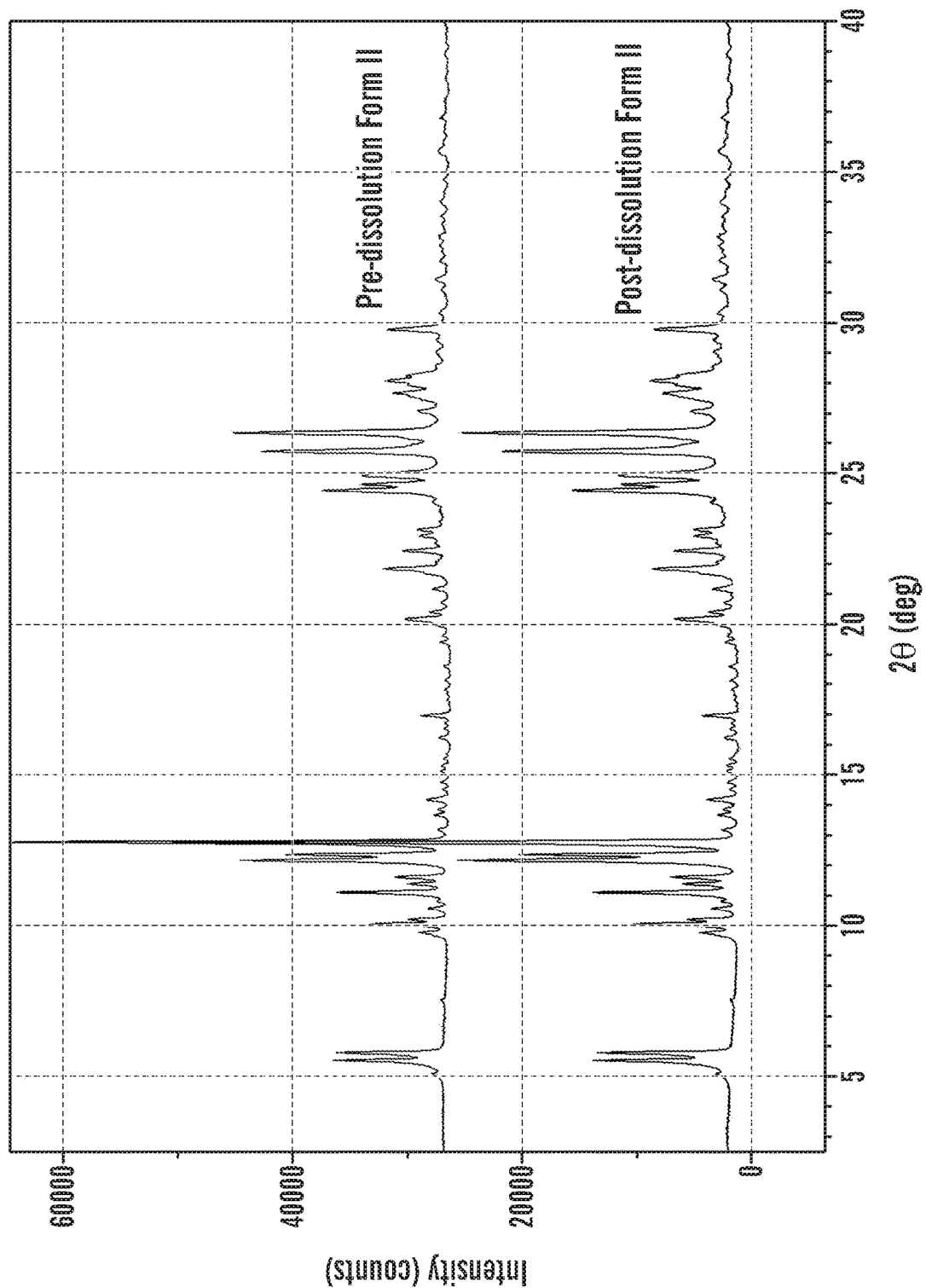
FIG. 21 is a set of pre and post dissolution treatment powder x-ray diffraction patterns for Form II EGCG:caffeine.
Figure 22:
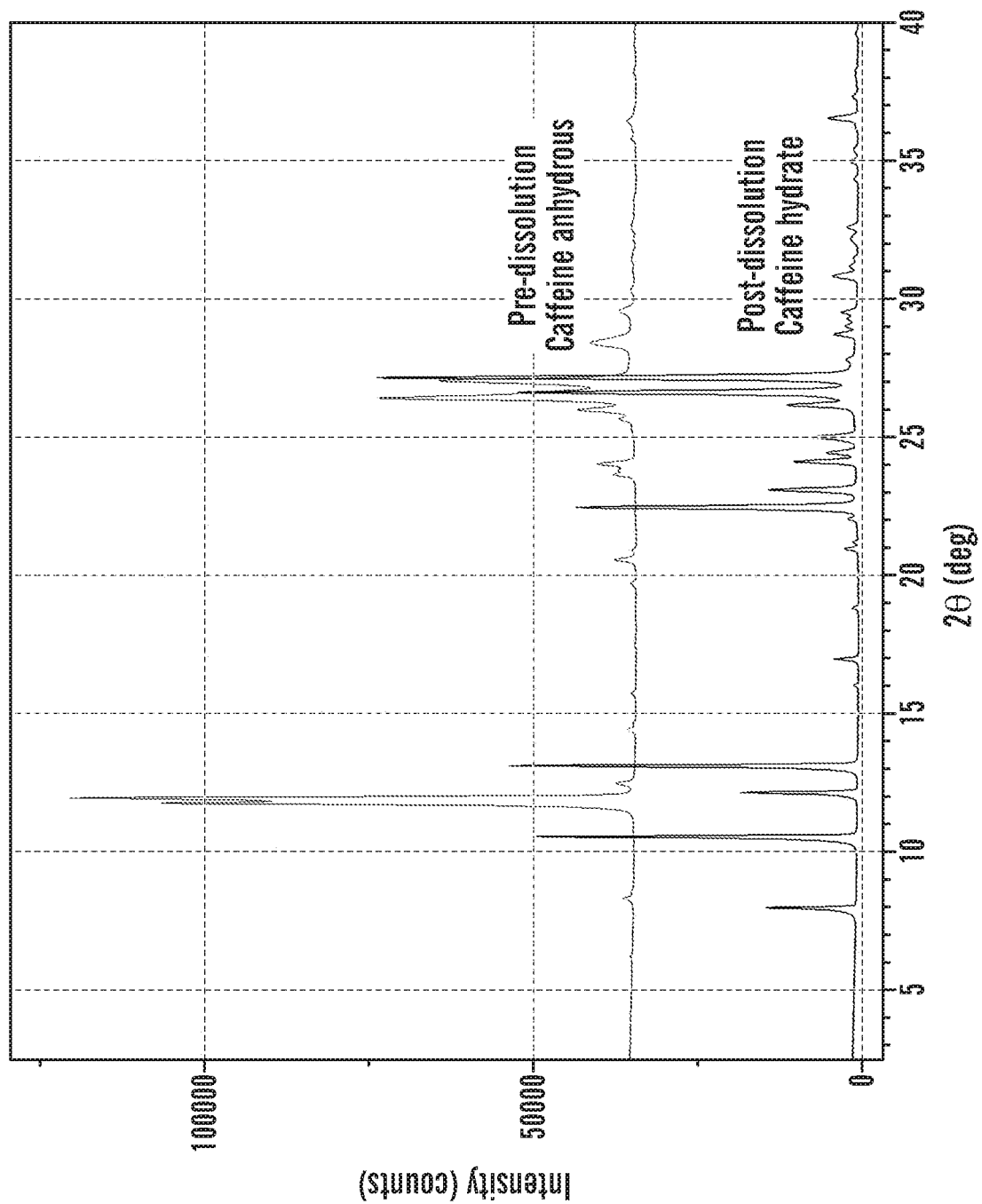
FIG. 22 is a set of a pre and post dissolution treatment powder x-ray diffraction patterns for caffeine.
Figure 23:
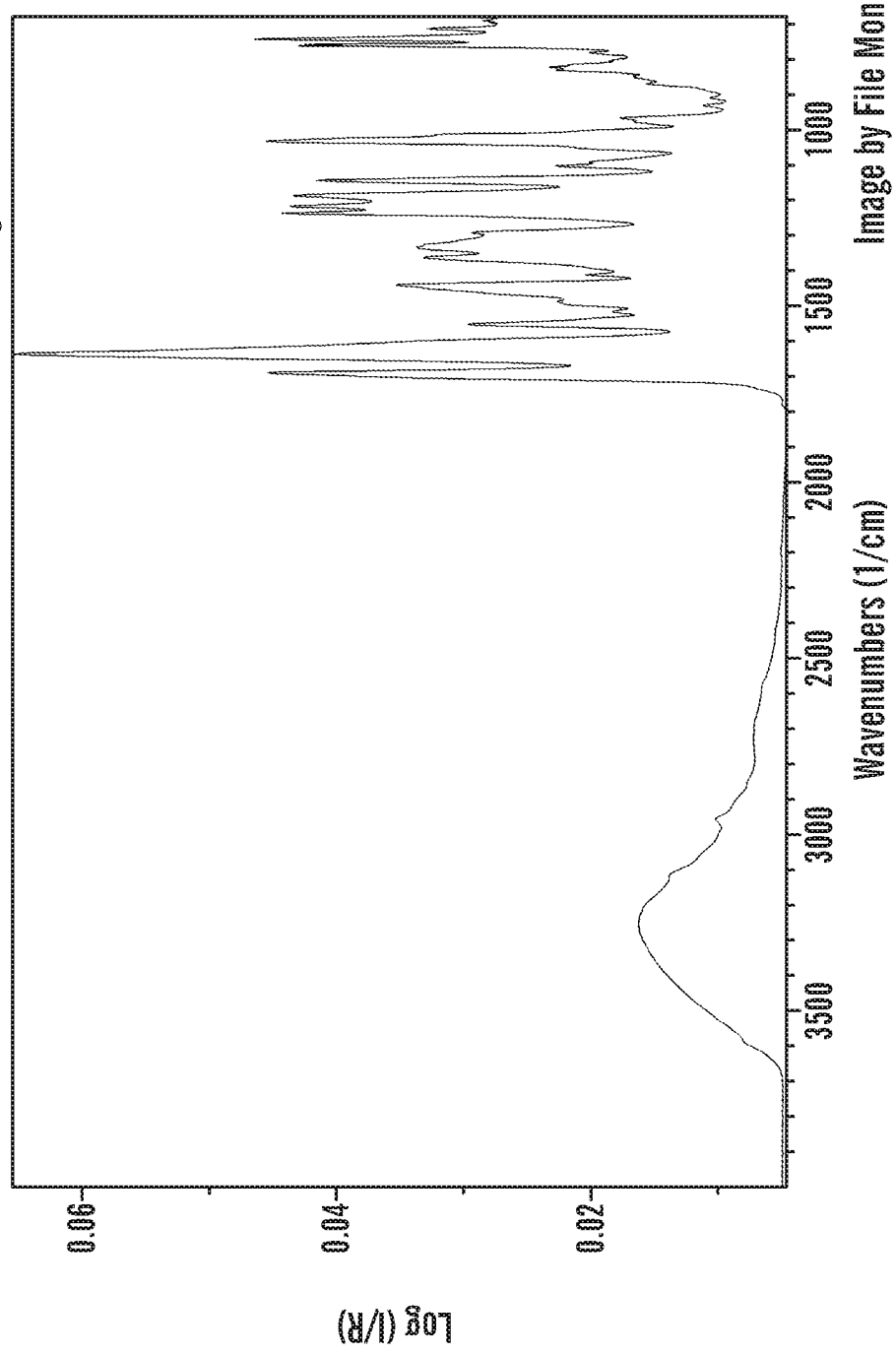
FIG. 23 is an IR spectrum for EGCG-caffeine cocrystal Form I.
Figure 24:
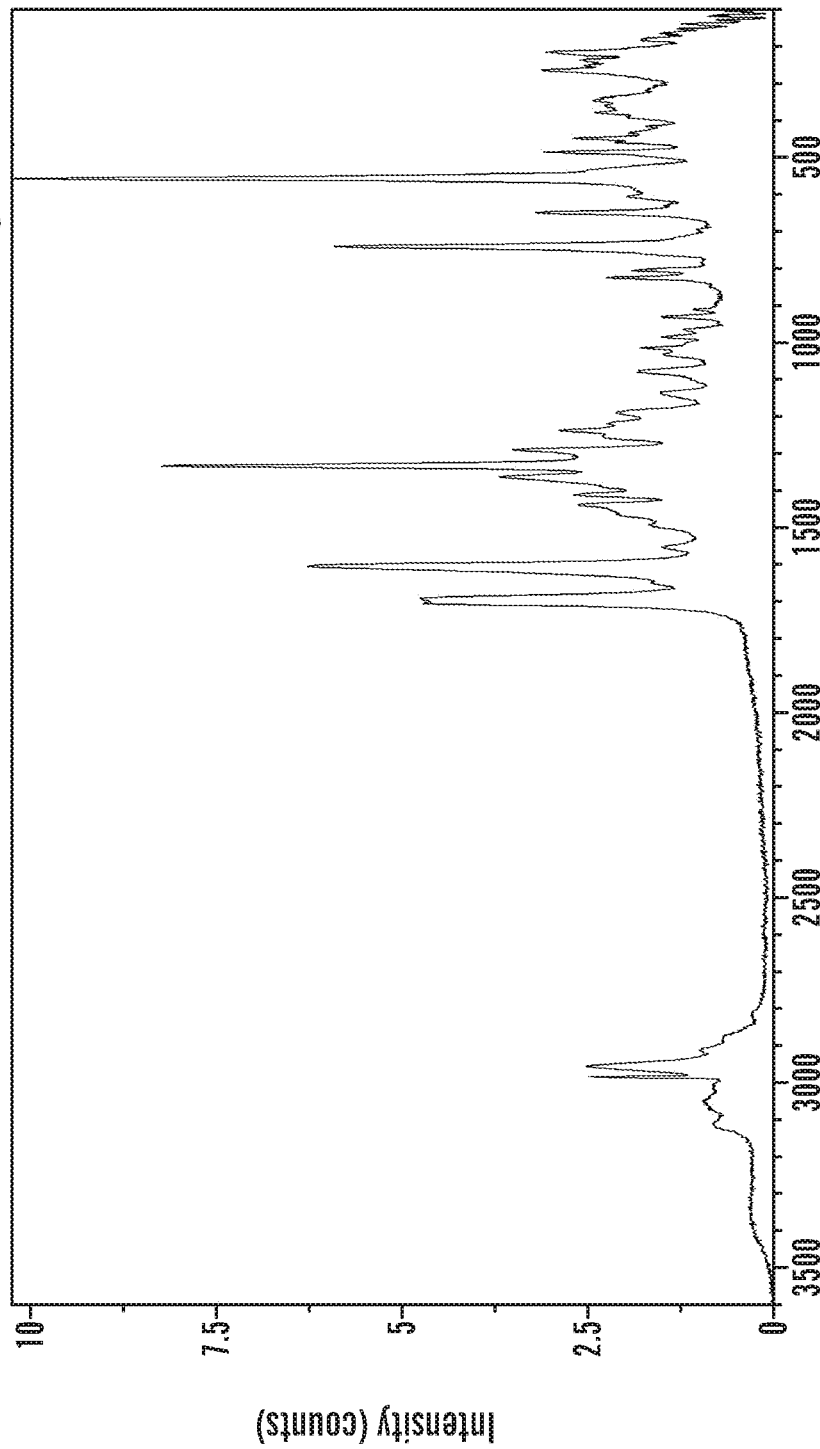
FIG. 24 is a Raman spectrum for EGCG-caffeine cocrystal Form I.
Figure 25:
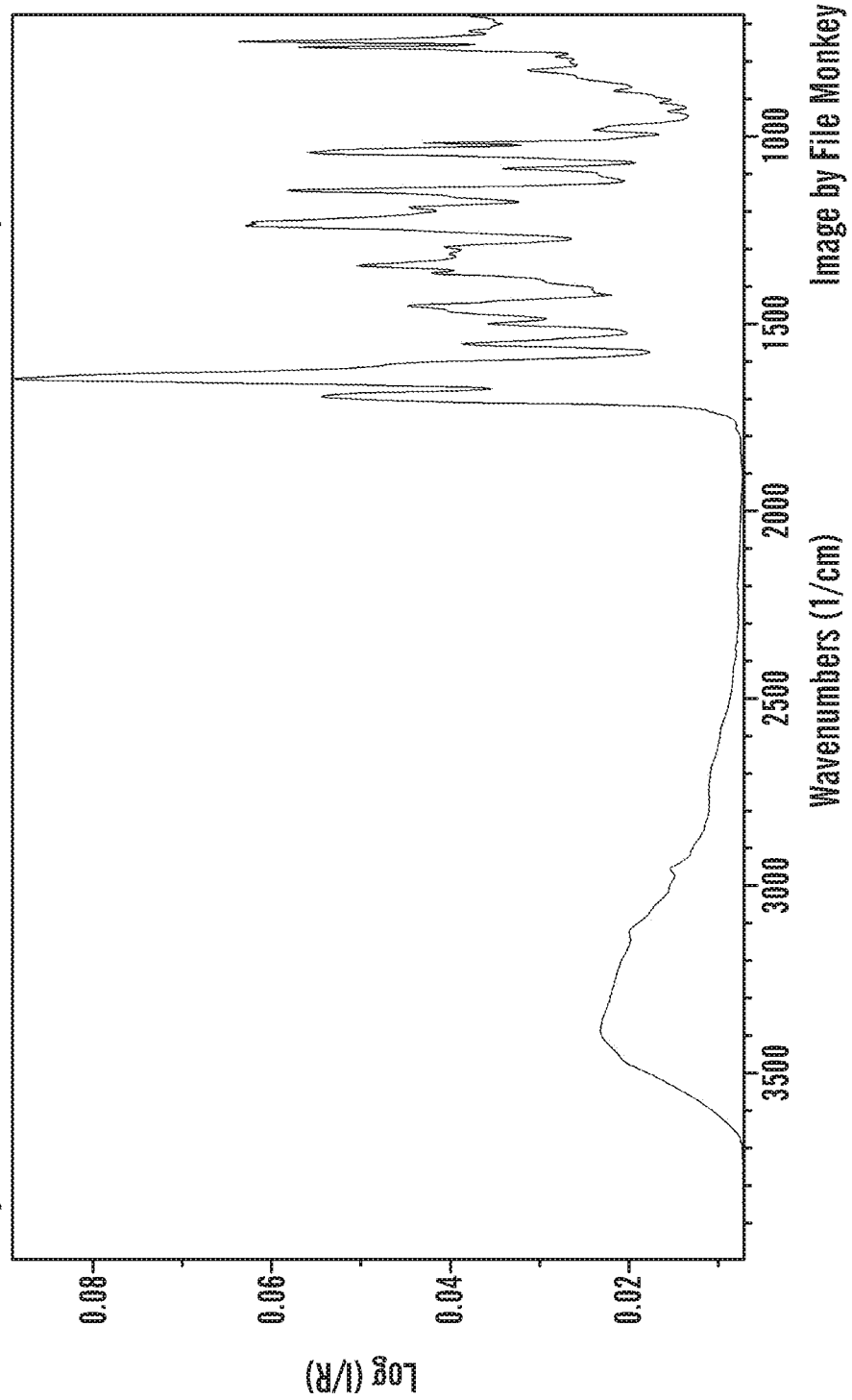
FIG. 25 is an IR spectrum for EGCG-caffeine cocrystal Form II (Preparation 3).
Figure 26:
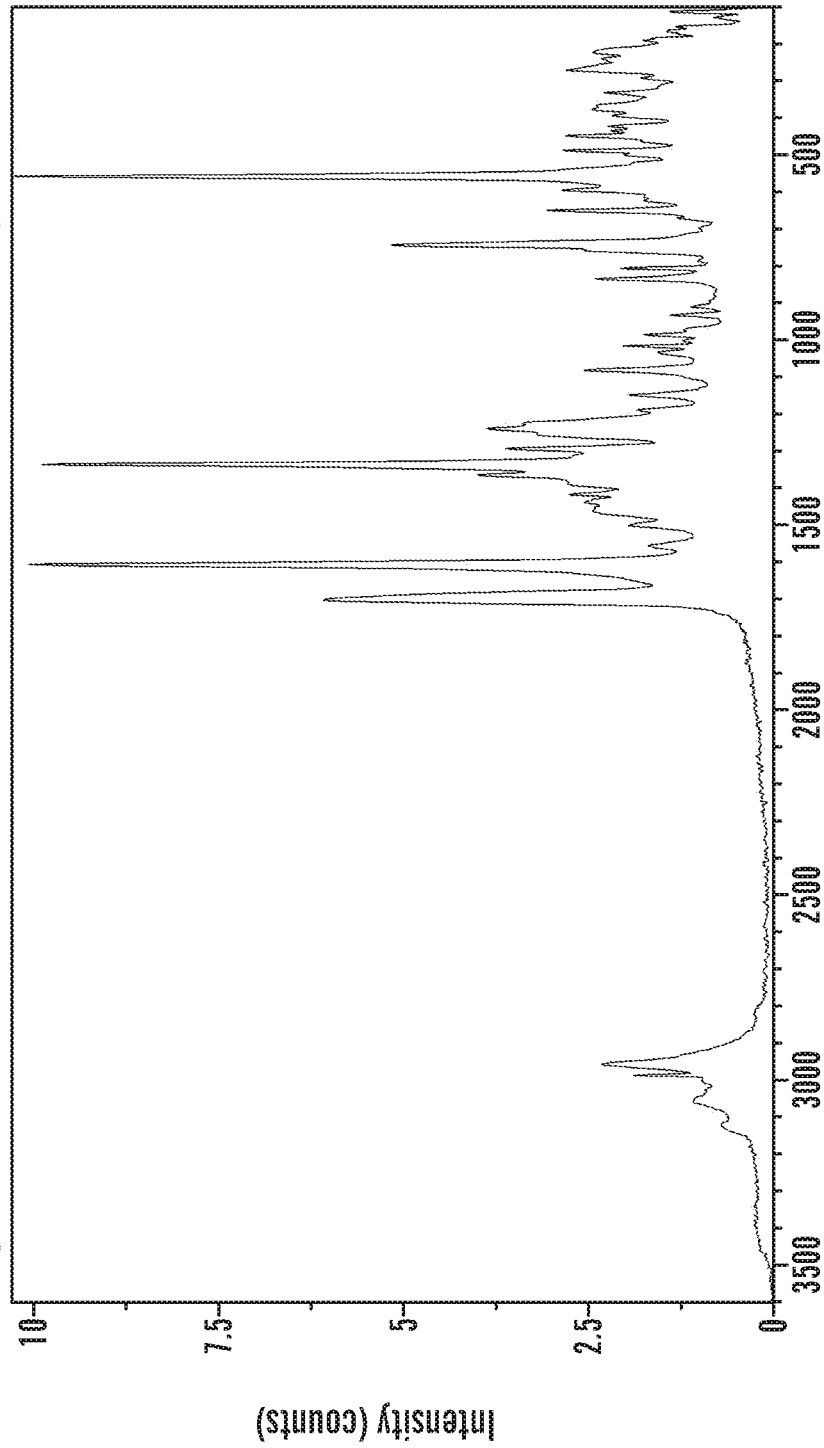
FIG. 26 is a Raman spectrum for EGCG-caffeine cocrystal Form II (Preparation 3).
Figure 27:
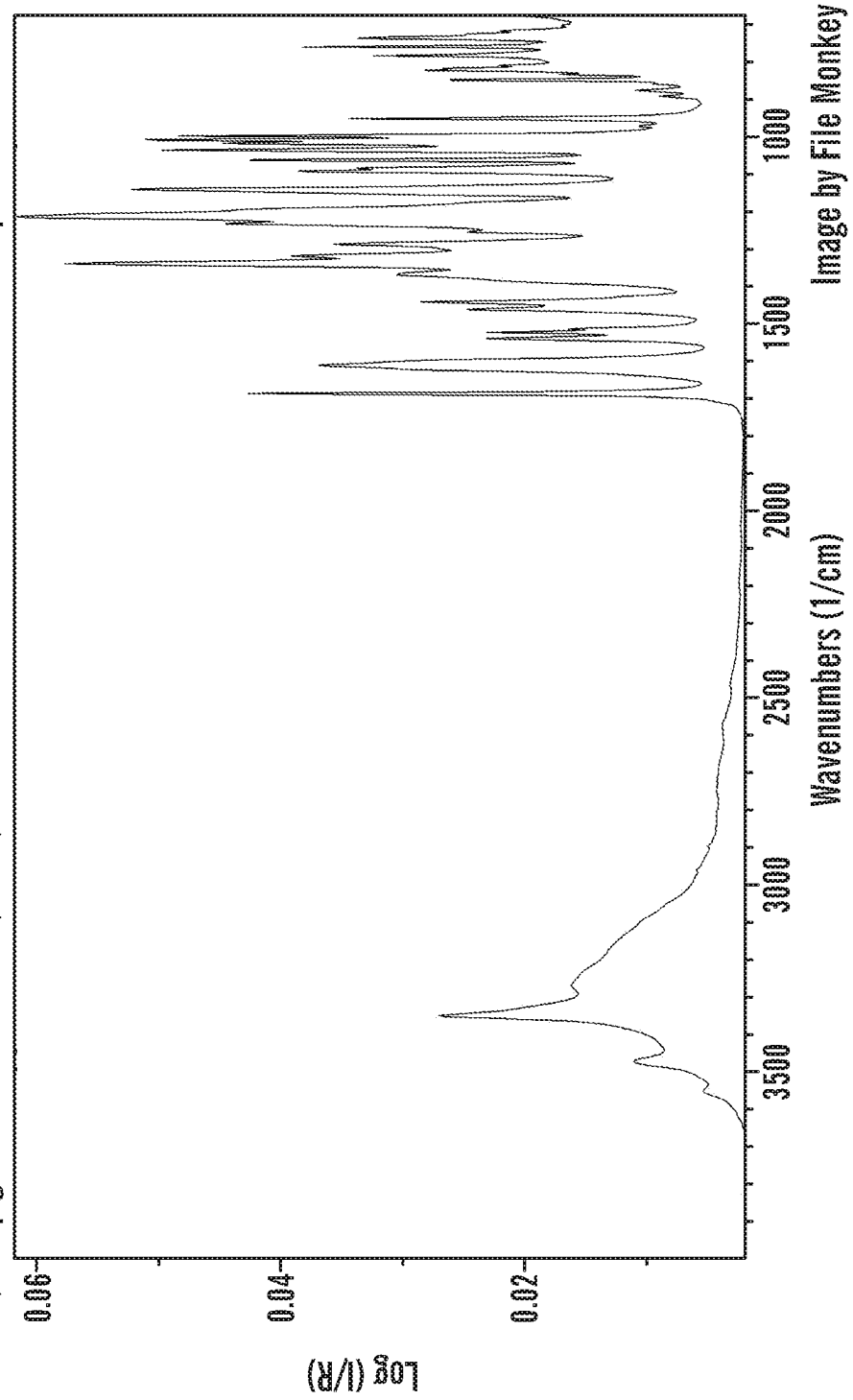
FIG. 27 is an IR spectrum for EGCG.
Figure 28:
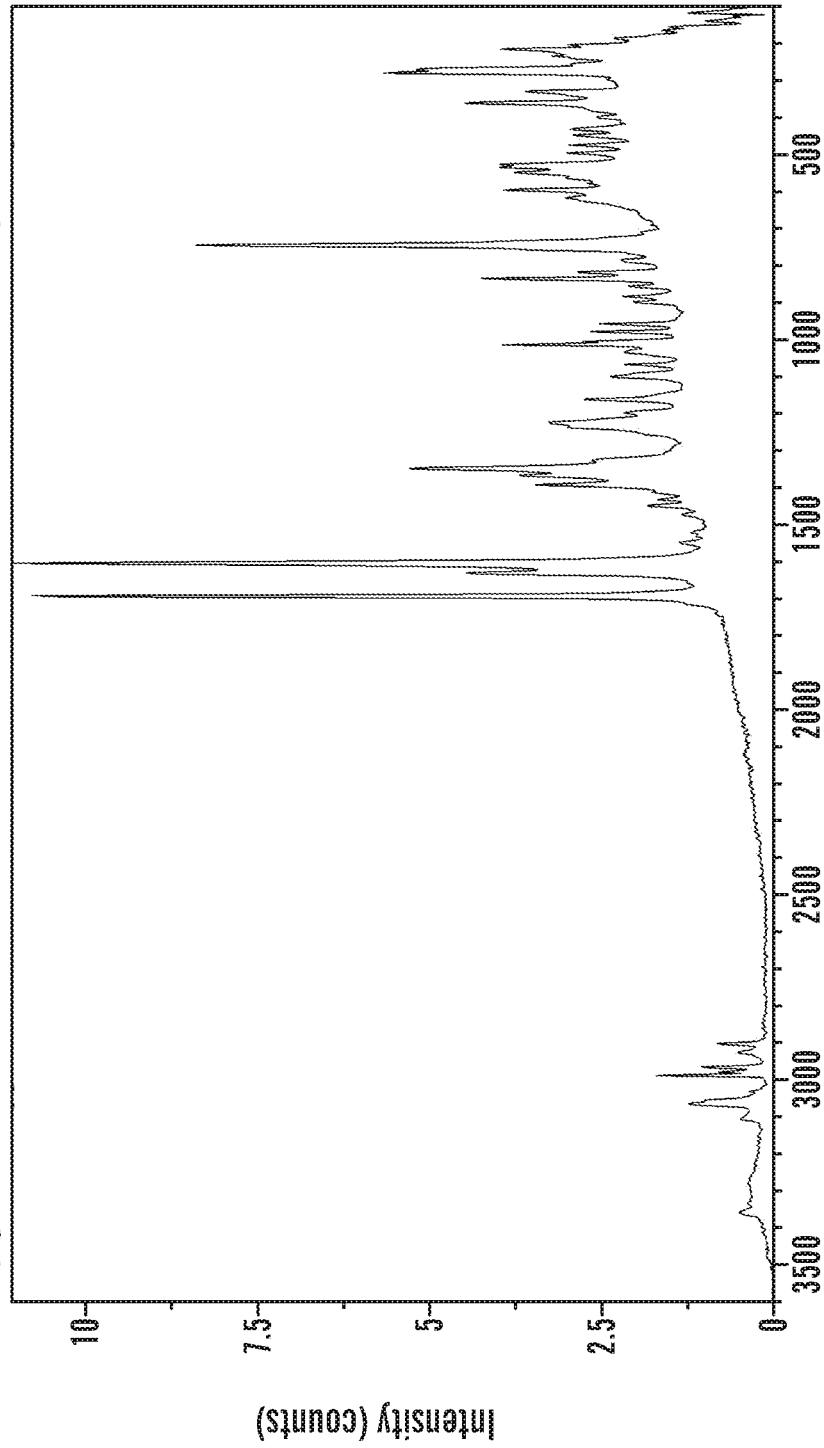
FIG. 28 is a Raman spectrum for EGCG.
Figure 29:
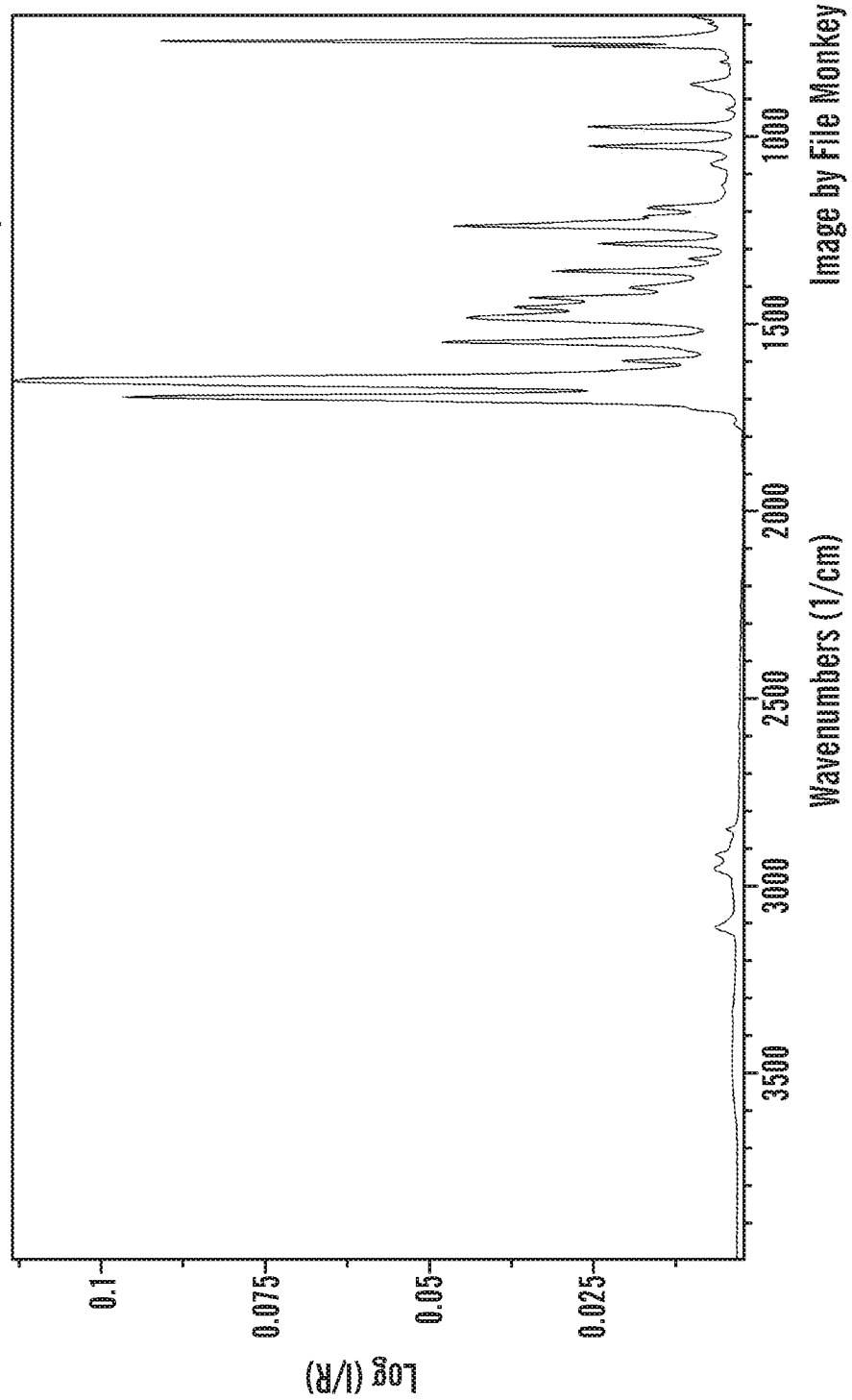
FIG. 29 is an IR spectrum for caffeine.
Figure 30:
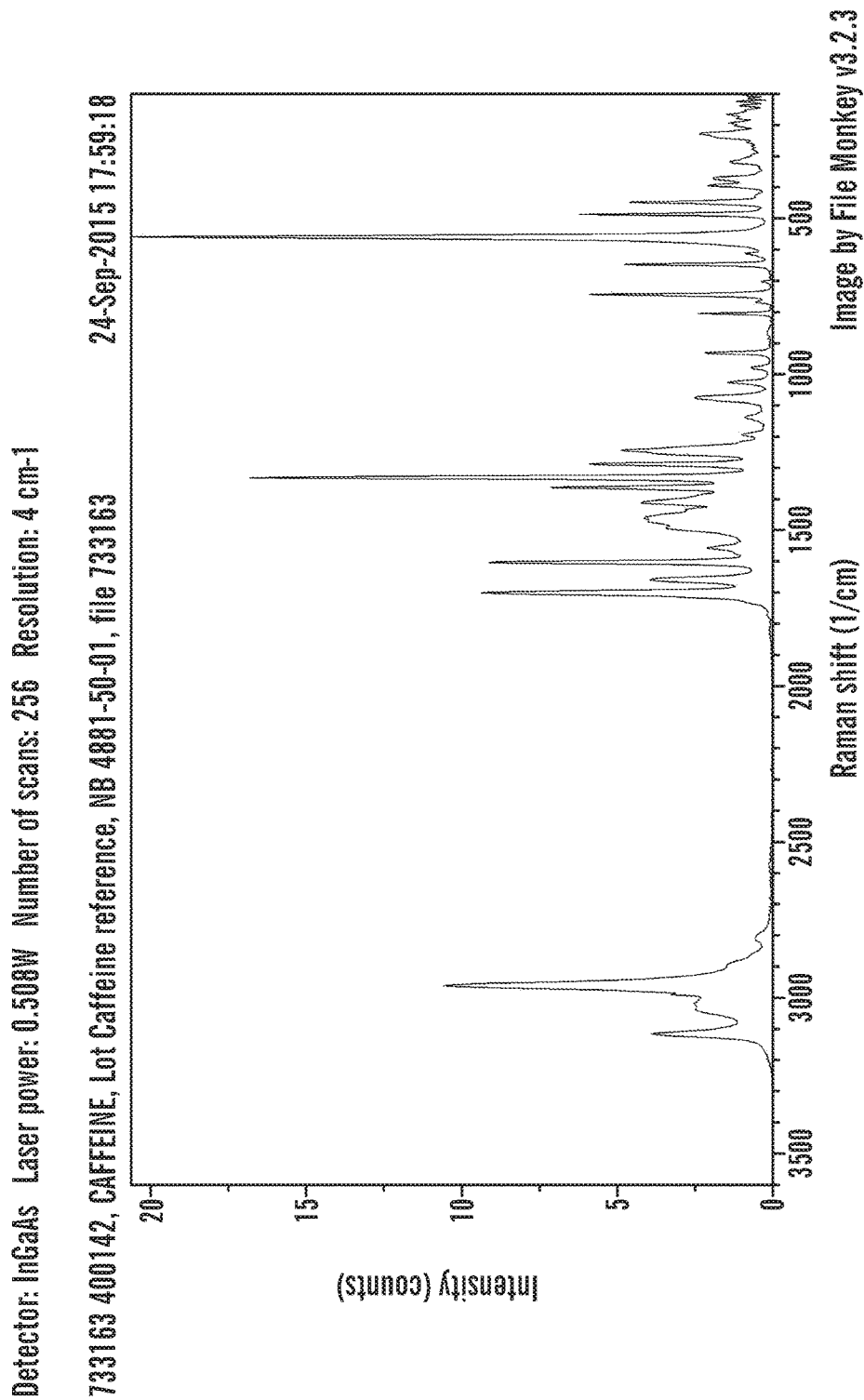
FIG. 30 is a Raman spectrum for caffeine.

FIGS. 21 and 22 show no change in Form II from the solids recovered post dissolution after 24 hours, whereas the anhydrous caffeine converted to the hydrate.

Example 5—RH Stability Study

Figure 16:
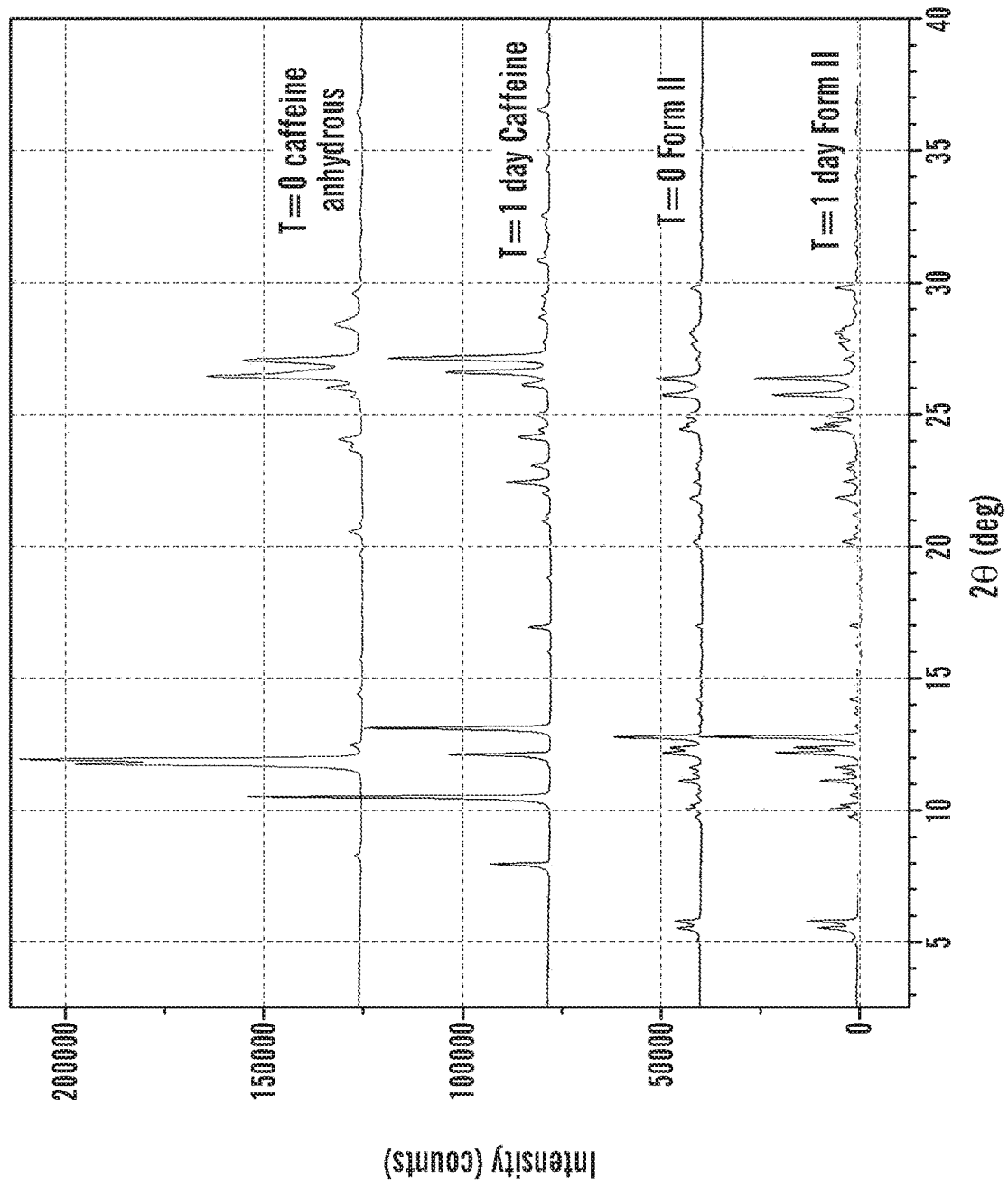
FIG. 16 shows x-ray diffraction patterns of caffeine and Form II EGCG:caffeine prior to exposure to 97% relative humidity at ambient temperature after 1 day.
Figure 17:
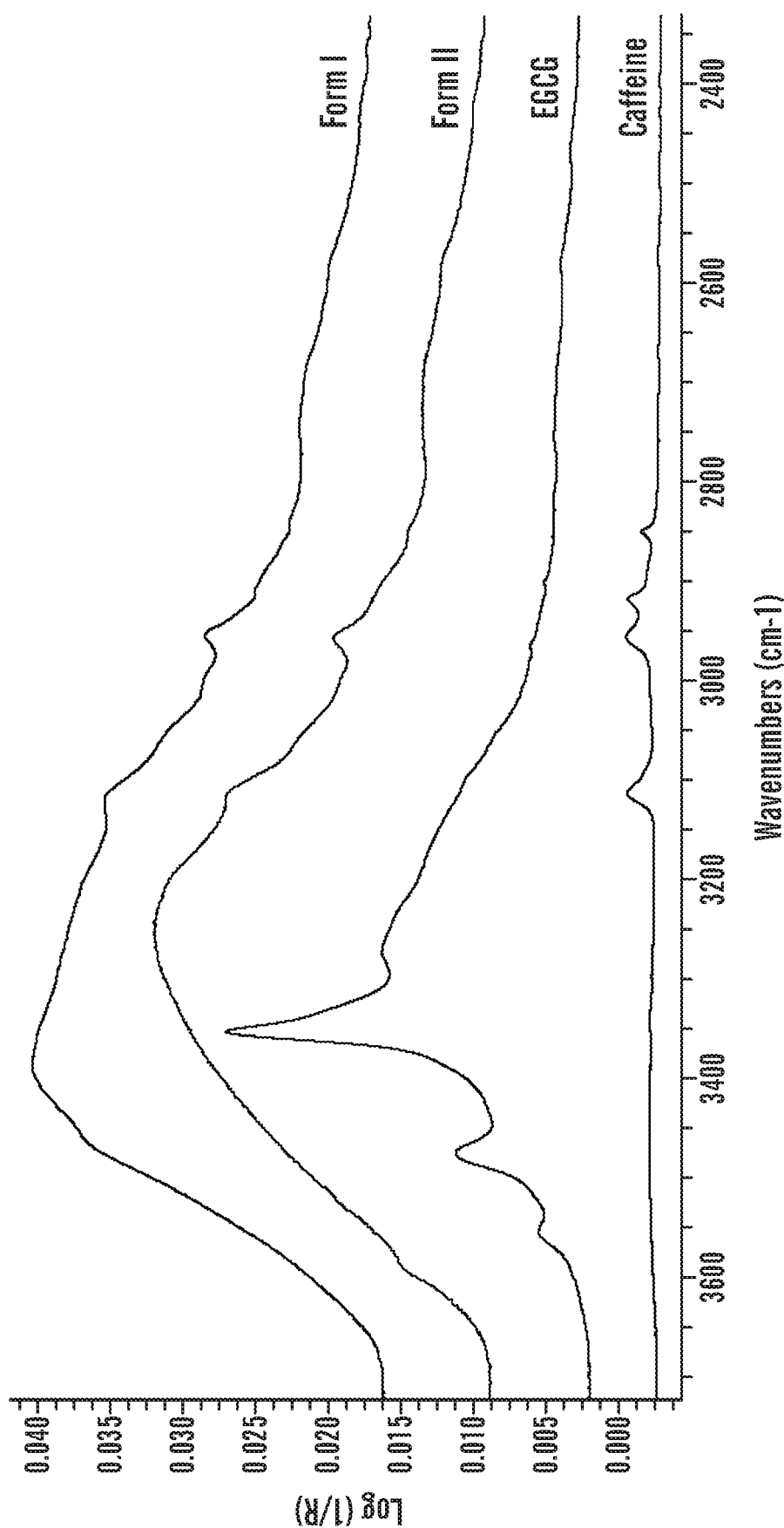
FIG. 17 is an expanded region overlay of infrared spectra of Forms I and II of EGCG:caffeine and EGCG and caffeine.
Figure 18:
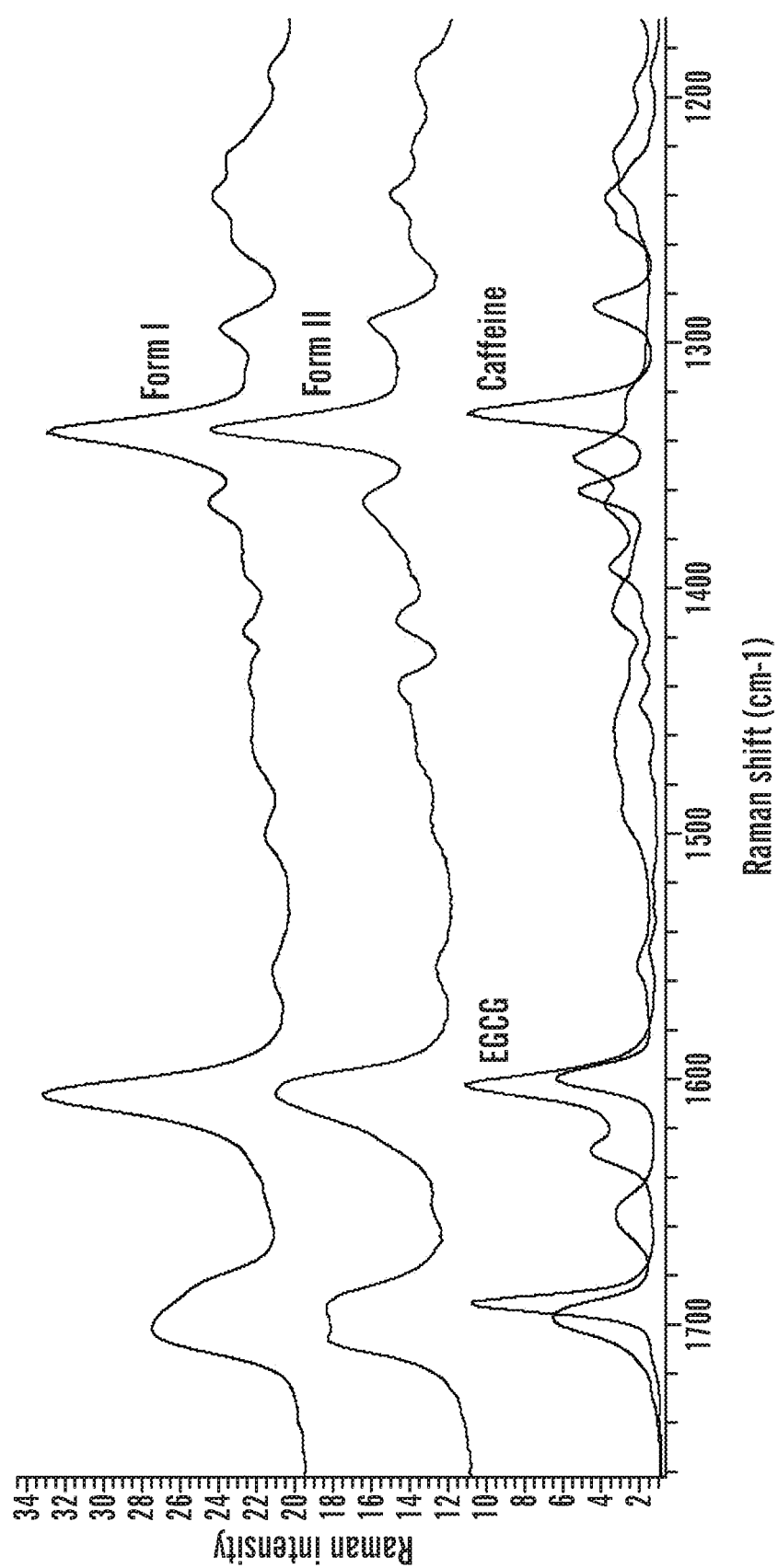
FIG. 18 is an expanded region overlay of FT-Raman spectra of Forms I and II of EGCG:caffeine and EGCG and caffeine.

About 50 mg of Form II (preparation one) was exposed to ~97% RH (ASTM Standard E, 104-85, 1996) for the specified period of time by placing an open vial containing the solids inside a capped container equilibrated to the given RH conditions. FIG. 16 shows the x-ray powder diffraction patterns of caffeine and Form II from preparation one, prior to exposure to 97% relative humidity and after 1 day at ambient temperature. Caffeine showed conversion to the hydrate whereas Form II (preparation two) did not appear to change.

Figure 15:
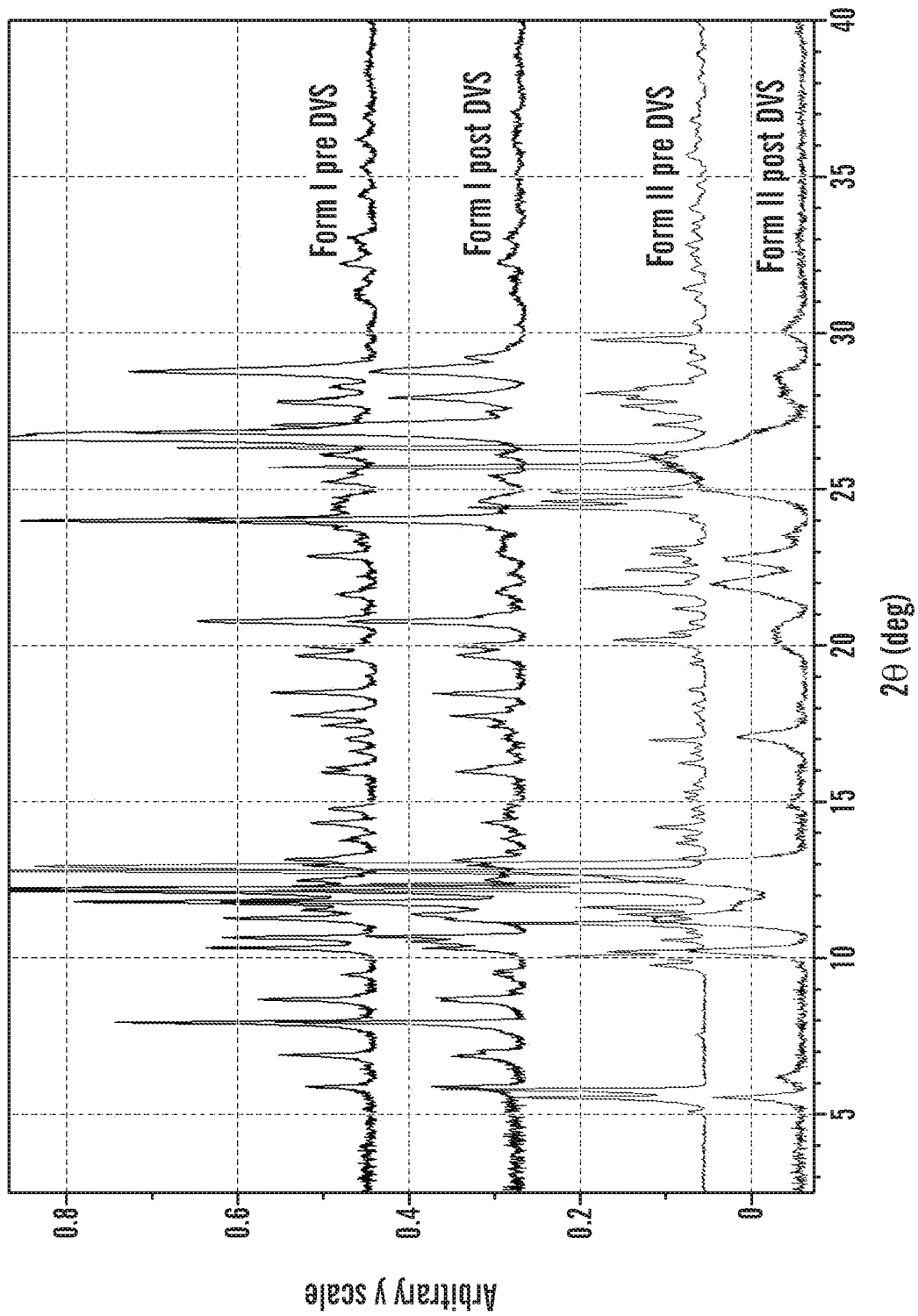
FIG. 15 shows the pre and post-DVS diffraction patterns of Forms I and II of EGCG:caffeine.

A DVS study on preparation two revealed, like Form I, Form II is hygroscopic. FIG. 15 shows the x-ray powder diffraction patterns of Form I and Form II pre and post DVS treatment. With Form II, 12.33% weight gain was recorded from 5-95% relative humidity and 11.24% weight loss from 95-5% relative humidity. Form I shows a weight gain of 10.95% from 5-95% relative humidity and weight loss of 10.83% from 95-5% relative humidity. For Form I, the pre- and post-DVS solids were consistent while for Form II, the post-DVS solids were disordered. This seems to be a difference between the two forms—i.e., Form I and Form II.

Example 6—Failed Attempts to Make Other Cocrystals with EGCG

Attempts to make other cocrystals with EGCG using the successful experimental conditions described supra were unsuccessful. These attempts utilized the following counterions in a 1:2 molar ratio (EGCG/counterion):theophylline, benzoic acid, citric acid, salicylic acid, hippuric acid, L-proline, taurine, piperazine, carbamazepine, pyrazine, and urea.

Although some embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. Form I of a cocrystal of epigallocatechin gallate and caffeine, wherein the cocrystal has an x-ray powder diffraction pattern with peaks at about 5.9°2θ and about 6.9°2θ, and wherein the molar ratio of caffeine to epigallocatechin gallate is 2 to 1.

2. The cocrystal according to claim 1 further comprising: an x-ray powder diffraction pattern with one or more peaks at about 7.9, 10.6, 11.3, or 16.9°2θ.

3. The cocrystal according to claim 1, wherein the cocrystal has a melting point of about 139° C.

4. Form II of a cocrystal of epigallocatechin gallate and caffeine, wherein the cocrystal has an x-ray powder diffraction pattern with two peaks between about 5.5°2θ and 5.8°2θ, and wherein the molar ratio of caffeine to epigallocatechin gallate is 2 to 1.

5. The cocrystal according to claim 4 further comprising: an x-ray powder diffraction pattern with one or more peaks at about 12.2, 12.4, or 12.8°2θ.

6. The cocrystal according to claim 4, wherein the cocrystal has a melting point of about 147° C.

7. A composition comprising a cocrystal according to claim 1 and an excipient.

8. A composition comprising a cocrystal according to claim 4 and an excipient.

* * * * *

UNITED STATES PATENT AND TRADEMARK OFFICE
CERTIFICATE OF CORRECTION

PATENT NO. : 10,813,938 B2  
APPLICATION NO. : 15/756213  
DATED : October 27, 2020  
INVENTOR(S) : Mehta et al.

Page 1 of 1

It is certified that error appears in the above-identified patent and that said Letters Patent is hereby corrected as shown below:

In the Claims

In Claim 2 at Column 14, Line 18, delete "16.9°2θ" and replace with --16.1°2θ--.

In Claim 4 at Column 14, Line 24, before "5.8°2°θ," insert --about--.

Signed and Sealed this  
Twenty-ninth Day of December, 2020

Andrei Iancu  
*Director of the United States Patent and Trademark Office*